United States Patent
Taghvaeeyan et al.

(10) Patent No.: US 12,023,149 B2
(45) Date of Patent: Jul. 2, 2024

(54) SENSING SYSTEM AND METHOD FOR MONITORING TIME-DEPENDENT PROCESSES

(71) Applicant: 3M INNOVATIVE PROPERTIES COMPANY, St. Paul, MN (US)

(72) Inventors: Saber Taghvaeeyan, Maple Grove, MN (US); Golshan Golnari, Maple Grove, MN (US); Mojtaba Kadkhodaie Elyaderani, St. Paul, MN (US); Robert W. Shannon, Stillwater, MN (US); Roger W. Barton, Afton, MN (US); Deepti Pachauri, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 849 days.

(21) Appl. No.: 17/252,415

(22) PCT Filed: Jul. 1, 2019

(86) PCT No.: PCT/IB2019/055608
§ 371 (c)(1),
(2) Date: Dec. 15, 2020

(87) PCT Pub. No.: WO2020/008339
PCT Pub. Date: Jan. 9, 2020

(65) Prior Publication Data
US 2021/0267488 A1  Sep. 2, 2021

Related U.S. Application Data

(60) Provisional application No. 62/693,364, filed on Jul. 2, 2018.

(51) Int. Cl.
*A61B 5/113* (2006.01)
*A61B 5/00* (2006.01)

(52) U.S. Cl.
CPC .......... *A61B 5/113* (2013.01); *A61B 5/7225* (2013.01); *A61B 5/7267* (2013.01); *A61B 5/7282* (2013.01)

(58) Field of Classification Search
CPC ..... A61B 5/113; A61B 5/7225; A61B 5/7267; A61B 5/7282
See application file for complete search history.

(56) References Cited

U.S. PATENT DOCUMENTS

2010/0292568 A1  11/2010  Droitcour
2014/0188006 A1  7/2014  Alshaer
(Continued)

FOREIGN PATENT DOCUMENTS

CA   3021049       10/2017
CN   107292350 A   10/2017
(Continued)

OTHER PUBLICATIONS

Liu, "Isolation Forest", 2008 Eight IEEE International Conference on Data Mining, Dec. 19, 2008, XP031423720, pp. 413-422.
(Continued)

*Primary Examiner* — Eric F Winakur
(74) *Attorney, Agent, or Firm* — Sriram Srinivasan

(57) ABSTRACT

Systems and methods for detecting the quality of signals captured by a sensor device monitoring a biological function. Sensor data associated with the sensor device is received, the sensor data representing time-series measurement samples of one or more parameters associated with the biological function, the sensor data including usable and unusable samples of the time-series measurements. Data representing two or more features of samples of the time-series measurements is extracted and filtered to reduce outliers in the extracted data based on an expected outlier (Continued)

ratio. A machine learning algorithm is then trained to identify events based on the filtered extracted data.

15 Claims, 26 Drawing Sheets

(56) References Cited

U.S. PATENT DOCUMENTS

| | | | |
|---|---|---|---|
| 2015/0164375 A1 | 6/2015 | Schindhelm | |
| 2016/0130656 A1 | 5/2016 | Whitney | |
| 2017/0367580 A1 | 12/2017 | Dimaio | |
| 2018/0018590 A1 | 1/2018 | Szeto et al. | |
| 2018/0189610 A1* | 7/2018 | Kandemir | G06F 18/2433 |
| 2020/0334228 A1* | 10/2020 | Matyska | G06N 20/00 |

FOREIGN PATENT DOCUMENTS

| | | |
|---|---|---|
| EP | 2589335 A2 | 5/2013 |
| EP | 3100675 | 12/2016 |
| WO | WO 2007-143535 | 12/2007 |
| WO | WO 2013-142908 | 10/2013 |
| WO | WO 2016-170005 | 10/2016 |
| WO | WO 2018-128976 | 7/2018 |

OTHER PUBLICATIONS

Bahense, "Benefits of anomaly detection using isolation forests",2016, 5 pages.
Freund, "A short introduction to boosting", Journal—Japense society for artificial intelligence, 1999, vol. 14, No. 5, pp. 771-780.
Sun, "Cost-sensitive boosting for classification of imbalanced data". Pattern Recognition, 2007, vol. 40, pp. 3358-3378.
Yao, "Boosting for transfer learning with multiple sources", IEEE Conferenceon Computer Vision and Pattern Recognition (CVPR), 2010,pp. 1855-1862.
International Search report for PCT International Application No. PCT/IB2019/055608 mailed on Oct. 16, 2019, 2 pages.

* cited by examiner

SENSING SYSTEM AND METHOD FOR MONITORING TIME-DEPENDENT PROCESSES

CROSS REFERENCE TO RELATED APPLICATIONS

This application is a national stage filing under 35 U.S.C. 371 of PCT/IB2019/055608, filed 1 Jul. 2019, which claims the benefit of Provisional U.S. Patent Application No. 62/693,364, filed 2 Jul. 2018, the entire disclosure of each of which is incorporated herein by reference.

TECHNICAL FIELD

This disclosure relates to systems and methods for monitoring time-dependent processes, and, in particular, to systems and methods for training sensor devices that monitor time-dependent processes.

BACKGROUND

Sensor devices are widely used in a range of different applications from health care to worker safety. Wearable devices may contain one or more sensors that measure a physiological signal such as body temperature, activity, breath, etc. The captured signals are then used to develop algorithms to detect, track, or predict a specific event. The accuracy and robustness of these algorithms depend on the "quality" and "quantity" of the signals provided during the algorithm development phase as well as during the operation phase. In early stages of deployment of a wearable device, for instance, where the amount of sensor data may not be adequate, it can be challenging to develop algorithms that accurately detect, track, or predict events based on the information received by the wearable device. Furthermore, low quality signals may impact the performance of the wearable device both at the training phase as well as during the test and operation phases, where the results may become less reliable.

Sensor devices may also be used in industrial settings. Many industrial processes are repetitive, if not cyclic. For instance, an automotive assembly line will start and stop, but cars on the assembly line pass the "underbody welding" station about once in every 30 to 200 seconds. The welding operation is repetitive; welding steps are not perfectly timed but are recurring. Errors occur from, for instance, material defects, problems in vision systems, or decays in the pressure applied by the welding machines.

In a plastic molding operation, material is injected into a mold such that the mold is moved to a curing step about once a minute. The injection process is not perfectly timed; a computer instead controls the process by monitoring temperature, pressure, and flow rates. Errors occur, for instance, because of variations in the injected material or because of variations in the heating and cool-down cycle of the mold.

In a thermal process, like smelting, the ore is melted in a furnace perhaps once per hour. The thermal cycle is variable because of changes in the weight of the charge and because of variations in the melting point of the materials. Errors occur, for instance, due to incomplete melting or uncontrolled vaporization.

Sensor devices may also be used in the home, for instance to monitor the health of an HVAC system. These systems are repetitive in the sense that heating and cooling systems are repeatedly engaged whenever a demand or control signal is applied to them. Errors occur in the system when, for instance, bearings wear out in a fan or where filtration systems become saturated.

Sensor devices may also be used for monitoring the health of a power distribution network, especially for load controls where power demand is cyclic or dependent on variations in weather patterns. Errors occur when the system cannot respond quickly enough to a new demand or when it loses the ability to regulate voltages due to errors in transformers or switching gear.

SUMMARY

The disclosure provides systems and methods for detecting the quality of signals captured by a sensor device. In a respiratory monitoring example, the sensor device is a wearable device that includes a sensor connected to a computing device. The sensor detects respiratory parameters and generates respective outputs representative of the respective respiratory parameters. The respiratory parameters may include amplitudes, rates, and durations of inhalation, exhalation, or both. The computing device is communicatively coupled (e.g., wirelessly connected) to the sensor. The computing device may be portable, such as, for example, a mobile phone, to allow the user to remain ambulatory while monitoring the respiratory parameters of the user. The computing device includes a processor that receives the output from the sensor. In some examples, the processor determines an occurrence of a breathing event based on an analysis of the output of the sensor. The breathing event may include the detection of a breathing state such as, for instance, a smooth breathing state (e.g., periods of improved breathing relative to average breathing activity), a hard-breathing state (e.g., periods of more labored breathing relative to average breathing activity), or the like. The computing device may store these breathing events and display, via a user interface, the breathing events to the user. In some examples, the computing device receives environmental information, user-provided information, or both and determines a trigger based on the received information. In some example, the trigger is associated with a respective breathing event. The computing device may store triggers and display, via a user interface, triggers to the user. In other examples, the computing device may cause the user interface to prompt the user to input triggers associated with a respective breathing event. The computing device may determine trends based on at least one of the sensor output, environmental information, user-provided information, breathing events, and triggers. The computing device may store trends and display, via a user interface, trends to the user. By storing and displaying breathing events, triggers, and trends, the systems and methods described herein may enable a user to identify triggers that cause improved breathing and worsened breathing.

The details of one or more examples are set forth in the accompanying drawings and the description below. Other features, objects, and advantages of the disclosure will be apparent from the description and drawings, and from the claims.

DETAILED DESCRIPTION

As noted above, wearable devices are widely used in a range of different applications from health care to worker safety. Wearable devices may contain one or more sensors that monitor a biological function. In some example approaches, the wearable device measures, for instance, a physiological signal such as body temperature, activity, breath, etc. The captured signals are then used to develop algorithms to detect, track, or predict a specific event. The accuracy and robustness of these algorithms depend on the "quality" and "quantity" of the signals provided during the algorithm development phase as well as during the operation phase. In early stages of development of a wearable device, for instance, where the amount and quality of sensor data may not be adequate, it can be challenging to develop algorithms that accurately detect, track, or predict events based on the information received by the wearable device.

The following disclosure describes systems and methods for training and using wearable devices and for detecting quality samples in the measurement samples obtained from the wearable devices. In one example approach, the wearable device measures breathing and motion. As one example, any of the systems and methods described herein may be implemented, individually or in combination, in a wearable device and cloud-based system for monitoring respiration as described in PCT/US2018/012048, entitled "SYSTEM AND METHOD FOR MONITORING RESPIRATION," filed Jan. 2, 2018, the entire content of which is incorporated herein by reference. Note that in this example, a wearable device that monitors breathing is described, but the methods presented here can be applied to other signals of a repetitive or cyclic nature captured by wearable devices, such as blood pressure, and to other types of sensors and systems, such as power grid monitoring systems and industrial process monitoring systems.

Figure 1:
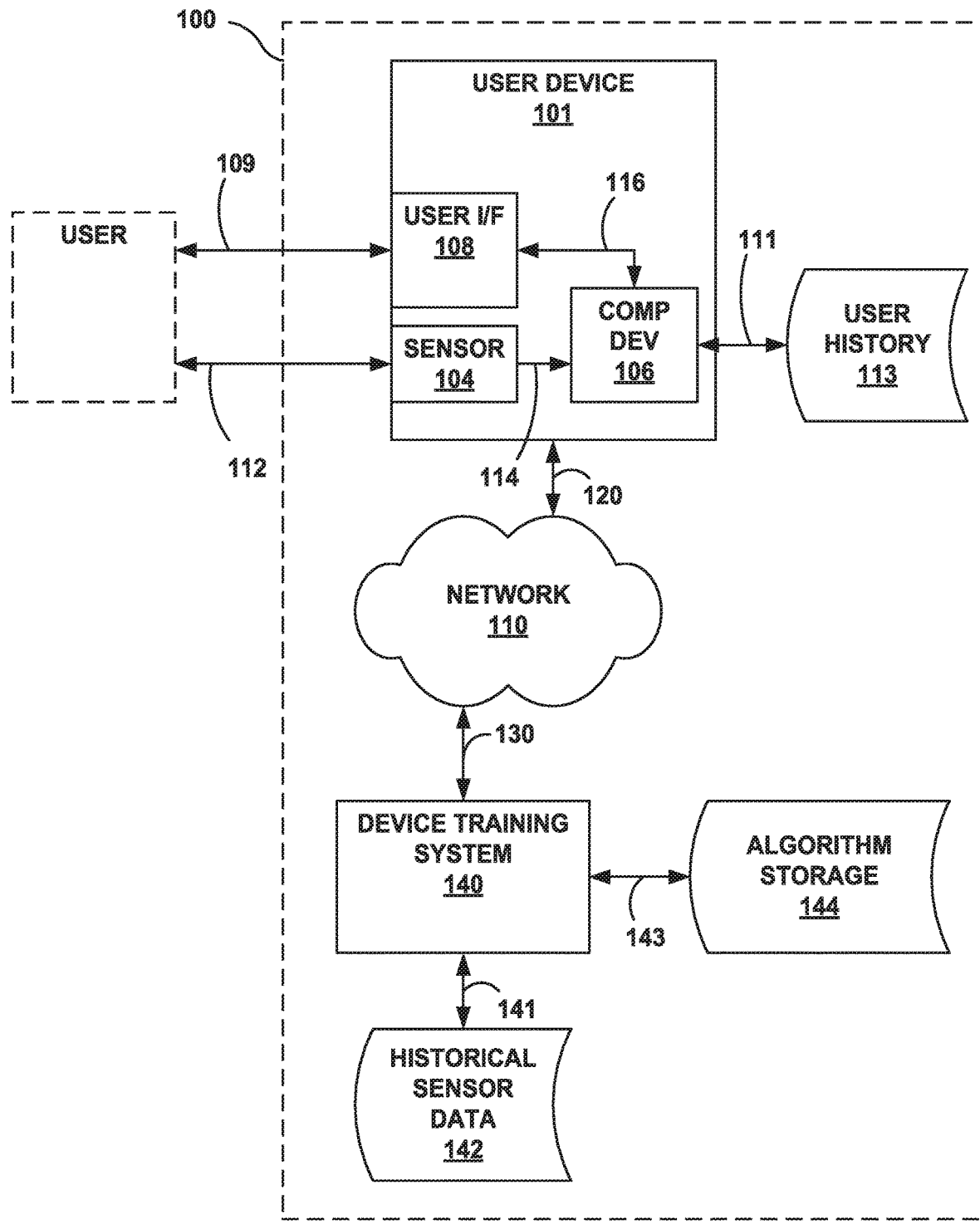
FIG. 1 is a block diagram illustrating a sensor device that monitors a biological function, in accordance with one aspect of the disclosure.

FIG. 1 is a block diagram illustrating a monitoring system used to monitor signals of a repetitive nature, such as a biological function or industrial process, in accordance with one aspect of the disclosure. In the example approach of FIG. 1, monitoring system 100 monitors cyclic biological signals representative of a user 102. User 102 may, for instance, by a human person that may or may not be ambulatory. In other examples, user 102 may be an animal, such as a domestic animal. In the example approach shown in FIG. 1, monitoring system 100 uses user device 101 to monitor the biological function of user 102.

In one example approach, user device 101 includes at least one sensor 104 that detects at least one signal indicative of characteristics of a cyclic biological function of user 102 (e.g., respiration or cardiac signals) at a sensor interface 112. For example, user device 101 may be affixed to a portion of the body of user 102 (e.g., the torso of user 102) or affixed to a garment worn by user 102 (e.g., an elastic band, a waist band, a bra strap, or the like). In some examples, user device 101 senses a movement of the torso of user 102 that results from respiration of user 102. In this way, user device 101 may detect the respiration of user 102 by respiratory inductance plethysmography (e.g., evaluating pulmonary ventilation by measuring the movement of the chest and abdominal wall). In other examples, user device 101 detects respiration signals of user 102 by other means. For example, user device 101 may include invasive or minimally invasive components, such as masks or mouthpieces coupled to the airway of user 102. Alternatively, or additionally, user device 101 may include other suitable sensors, or combination of sensors, to detect respiration of user 102, such as strain gauge sensors, pressure sensors, accelerometers, gyroscopes, displacement sensors, acoustic sensors, ultrasonic sensors, flow sensors, optical sensors, including cameras and/or infrared sensors, or combinations thereof. Alternatively, or additionally, user device 101 may include sensors or combinations of sensors suitable for measuring cardiac or brain activity.

In one example approach, user device 101 detects signals representing time-series measurement samples of one or more parameters associated with the biological function being monitored by sensor 104 at sensor interface 112 either intermittently or in real time. User device 101 may, for instance, enable monitoring system 100 to track the respiration signals of user 102. In one such example approach, sensor data captured from user 102 is stored over a link 111 to user history storage 113.

User device 101 includes any suitable computing device 106, such as a smartphone, a computerized wearable device (e.g., a watch, eyewear, ring, necklace, or the like), a tablet, a laptop, a desktop, or of the like. In some examples, the computing device and sensor 104 are two separate devices. In other examples, the computing device and sensor 104 are components of the same device.

In one example approach, the output from sensor 104 is received by computing device 106 via link 114. In one such example approach, a processor of computing device 106 determines an occurrence of a breathing event based on the output. For example, the processor may communicate with one or more modules of computing device 106 to determine the occurrence of the breathing event such as detection of a breathing state based on the output. Computing device 106 may include a data storage to store sensor 104 output, detected events, or both (e.g., respiration or other such data). By receiving sensor 104 output, determining breathing events based on the output, and storing respiration data, computing device 106 may enable monitoring system 100 to track sensor data of user 102 over time.

In one example approach, link 114 includes any suitable wired connection (e.g., metal traces, fiber optics, Ethernet, or the like), a wireless connection (e.g., personal area network, local area network, metropolitan area network, wide area network, or the like), or a combination of both. For example, sensor 104 may include a communications unit that includes a network interface card, such as an Ethernet card, an optical transceiver, a radio frequency transceiver, a Bluetooth® interface card, WiFi™ radios, USB, or any other type of device that can send and receive information. In this way, sensor 104 generates an output representative of at least one respiratory parameter (e.g., data representative of a respiratory signal) that is received by computing device 106.

Computing device 106 is communicatively coupled (e.g., connected) to user interface 108 via link 116. Link 116 may be the same or similar to link 114 discussed above. User interface 108 may include a graphical user interface (GUI), a display, a keyboard, a touchscreen, a speaker, a microphone, a gyroscope, an accelerometer, a vibration motor, or the like. In some examples, computing device 106 and user interface 108 are components of the same device, such as a mobile phone, a tablet, a laptop, or the like. In other examples, computing device 106 and user interface 108 are separate devices.

In one example approach, computing device 106 includes one or more output components that generate tactile output, audio output, video output, or the like that is received by user interface 108 to communicate information to user 102 or another entity. In this way, user interface 108 may notify user 102 of an occurrence of a breathing event. As one example, user interface 108 may receive an indication of the occurrence of a breathing event from computing device 106 and display on a display of user interface 108 information representative of the occurrence of the breathing event to user 102. Similarly, user interface 108 includes one or more input components that receive tactile input, kinetic input, audio input, optical input, or the like from user 102 or another entity 108. In this way, user interface 108 may receive user input from user 102 and send user input to computing device 106. For example, user 102 may provide user input to user interface 108, which communicates the user input to computing device 106. The user input (e.g., user data) includes, for example, information about age, gender, height, weight, and medical conditions; information associated with an occurrence of a breathing event, information associated with triggers generally or triggers of a respective occurrence of a breathing event, and the like. By communicatively coupling output components and input components of computing device 106 to user interface 108, user 102 (or another entity) may interact with computing device 106.

Computing device 106 includes any suitable computing device, such as a smartphone, a computerized wearable device (e.g., a watch, eyewear, ring, necklace, or the like), a tablet, a laptop, a desktop, or of the like. In some examples, computing device 106 and sensor 104 are two separate devices. In other examples, computing device 106 and sensor 104 are components of the same device. The output from sensor 104 is received by a processor of computing device 106. The processor of computing device 106 determines an occurrence of a breathing event based on the output. For example, the processor may communicate with one or more modules of computing device 106 to determine the occurrence of the breathing event such as detection of a breathing state based on the output. Computing device 106 may include a data storage to store sensor 104 output, the determined breathing event, or both (e.g., respiration data). By receiving sensor 104 output, determining breathing events based on the output, and storing respiration data, computing device 106 may enable respirator monitoring system 100 to track respiration data of user 102 over time.

Computing device 106 is communicatively coupled (e.g., connected) to user interface 108 via link 116. Link 116 may be the same or similar to link 114 discussed above. User interface 108 may include a graphical user interface (GUI), a display, a keyboard, a touchscreen, a speaker, a microphone, a gyroscope, an accelerometer, a vibration motor, or the like. In some examples, computing device 106 and user interface 108 are components of the same device, such as a mobile phone, a tablet, a laptop, or the like. In other examples, computing device 106 and user interface 108 are separate devices. Computing device 106 includes one or more output components that generate tactile output, audio output, video output, or the like that is received by user interface 108 to communicate information to user 102 or another entity. In this way, user interface 108 may notify user 120 of an occurrence of a breathing event. As one example, user interface 108 may receive an indication of the occurrence of a breathing event from computing device 106 and display on a display of user interface 108 information representative of the occurrence of the breathing event to user 102. Similarly, computing device 106 includes one or more input components that receive tactile input, kinetic input, audio input, optical input, or the like from user 102 or another entity via user interface 108. In this way, user interface 108 may receive user input from user 102 and send user input to computing device 106. For example, user 102 may provide user input to user interface 108, which communicates the user input to computing device 106. The user input (e.g., user data) includes, for example, information about age, gender, height, weight, and medical conditions; information associated with an occurrence of a breathing event, information associated with triggers generally or triggers of a respective occurrence of a breathing event, and the like. By communicatively coupling output components and input components of computing device 106 to user interface 108, user 102 (or another entity) may interact with computing device 106. Although user device 101 of FIG. 1 includes sensor 104, computing device 106, and user interface 108, in some example approaches, user device 101 may include fewer or more components.

In one example approach, as shown in FIG. 1, sensor 104, computing device 106, and user interface 108 are optionally communicatively coupled to network 110. In other examples, fewer components (e.g., only computing device 106) may be coupled to network 110. Network 110 represents any public or private communication network, for instance, cellular, WiFi®, or other types of networks for transmitting data between computing systems, servers, and computing devices. Sensor 104, computing device 106, and user interface 108 may each be operatively coupled to network 110 using network link 120. Network link 120 may be any type of network connections, such as wired or wireless connections as discussed above. Network 110 may provide selected devices, such as sensor 104, computing device 106, and user interface 108 with access to the Internet, and may allow sensor 104, computing device 106, and user interface 108 to communicate with each other. For example, rather than communicating via link 114, sensor 104 and computing device 106 may communicate via network link 120. Similarly, rather than communicating via link 116, computing device 106 and user interface may communicate via network link 120. Additionally, sensor 104 may communicate directly with user interface 108 via network link 120.

In one example approach, user device 101 is communicatively coupled (e.g., connected) through network 110 to a device training system 140 via network link 130. In one such example approach, device training system 140 receives sensor data from user devices 101 and stores the sensor data to historical sensor data storage 142. The data may, for instance, be pushed to historical sensor data storage 142 by user device 101 or it may be retrieved from user history storage 113 by device training system 140 before being stored in historical sensor data storage 142. Network link 130 may be the same or substantially similar to network link 120 discussed above. Device training system 140 may also connected to algorithm storage 144 via a link 143.

Figure 2:
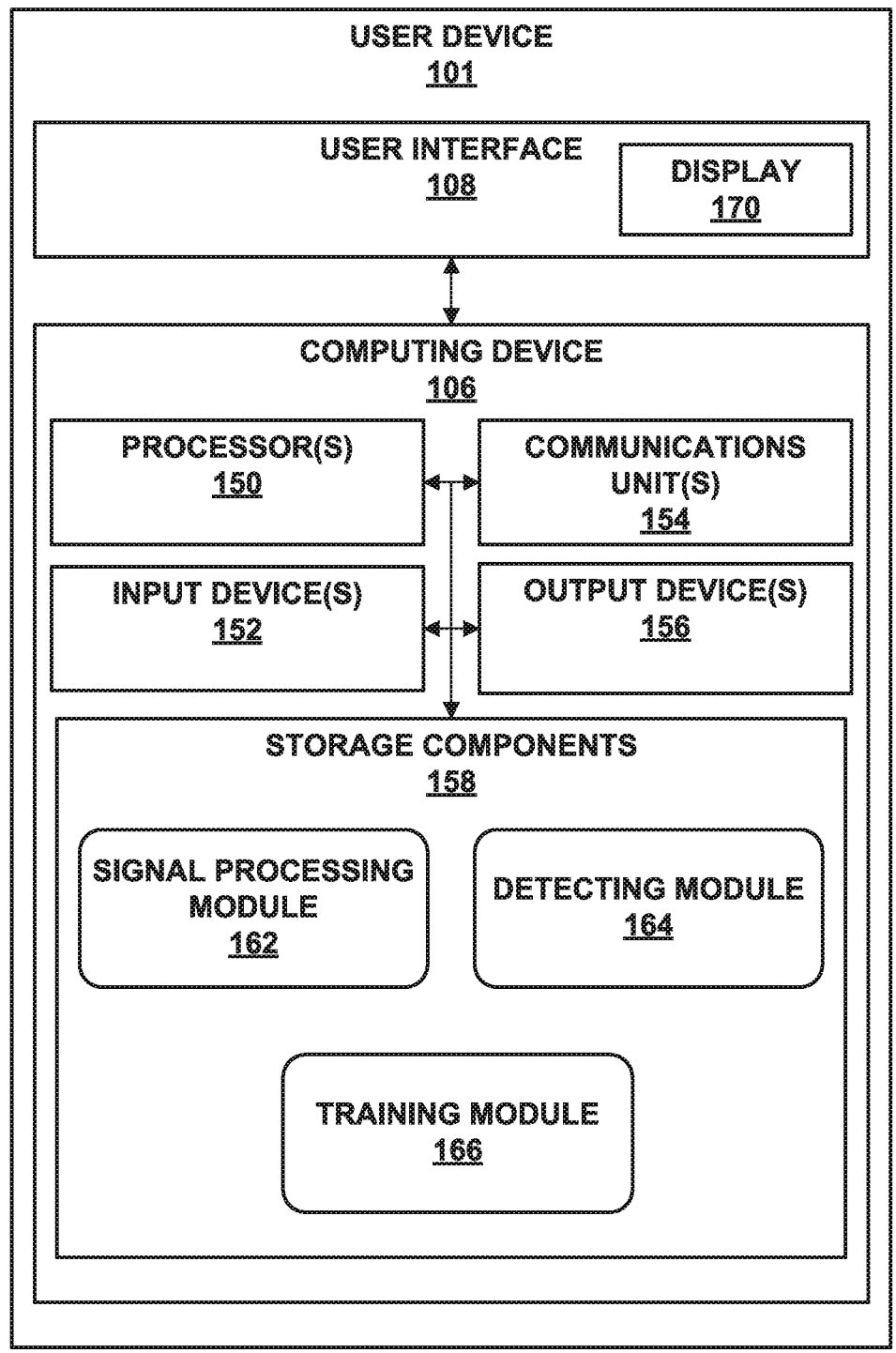
FIG. 2 is a schematic and conceptual diagram illustrating an example user device that includes a computing device and a user interface, in accordance with one aspect of the disclosure.

FIG. 2 is a schematic and conceptual diagram illustrating an example user device that includes a computing device and a user interface, in accordance with one aspect of the disclosure. In one example approach, computing device 106 includes one or more processors 150, one or more input devices 152, one or more communications units 154, one or more output devices 156, and one or more one or more storage components 158. In some examples, the one or more storage components 158 include a signal processing module 160, a detecting module 162, and a training module 164. In other examples, computing device 106 may include additional components or fewer components than those illustrated in FIG. 2.

One or more processors 150 are configured to implement functionality, process instructions, or both for execution within computing device 106. For example, processors 150 may be capable of processing instructions stored within one or more storage components 158. Examples of one or more processors 150 may include, any one or more of a microprocessor, a controller, a digital signal processor (DSP), an application specific integrated circuit (ASIC), a field-programmable gate array (FPGA), or equivalent discrete or integrated logic circuitry.

Computing device 106 also includes one or more input devices 152. Input devices 152, in some examples, are configured to receive input from a user through tactile, audio, or video sources. Examples of input devices 152 include a mouse, a button, a keyboard, a voice responsive system, video camera, microphone, touchscreen, or any other type of device for detecting a command from a user. In some example approaches, user interface 108 includes all input devices 152 employed by computing device 106.

Computing device 106 further includes one or more communications units 154. Computing device 106 may utilize communications units 154 to communicate with external devices (e.g., sensor 104, or user interface 108) via one or more networks, such as one or more wired or wireless networks. Communications units 154 may include a network interface card, such as an Ethernet card, an optical transceiver, a radio frequency transceiver, or any other type of device that can send and receive information. Communications units 154 may also include WiFi™ radios or a Universal Serial Bus (USB) interface. In some examples, computing device 106 utilizes communications units 154 to wirelessly communicate with an external device such as a server.

Computing device 106 may further include one or more output devices 156. Output devices 156, in some examples, are configured to provide output to a user using, for example, audio, video or tactile media. For example, output devices 156 may include display 170 of user interface 108, a sound card, a video graphics adapter card, or any other type of device for converting a signal into an appropriate form understandable to humans or machines. In some example approaches, user interface 108 includes all output devices 156 employed by computing device 106.

One or more storage components 158 may be configured to store information within computing device 106 during operation. One or more storage components 158, in some examples, include a computer-readable storage medium or computer-readable storage device. In some examples, one or more storage components 158 include a temporary memory, meaning that a primary purpose of one or more storage components 158 is not long-term storage. One or more storage components 158, in some examples, include a volatile memory, meaning that one or more storage components 158 does not maintain stored contents when power is not provided to one or more storage components 158. Examples of volatile memories include random access memories (RAM), dynamic random-access memories (DRAM), static random-access memories (SRAM), and other forms of volatile memories known in the art. In some examples, one or more storage components 158 are used to store program instructions for execution by processors 150. One or more storage components 158, in some examples, are used by software or applications running on computing device 106 to temporarily store information during program execution.

In some examples, one or more storage components 158 may further include one or more storage components 158 configured for longer-term storage of information. In some examples, one or more storage components 158 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 106 may include signal processing module 162, detecting module 164, and training module 166. In one such example approach, signal processing module 162 analyzes the data received from sensor 104, processing the data to improve the quality of the sensor data. Detecting module 164 analyzes the sensor data to detect events representative of, for instance, a biological function of user 102. Training module 166 modifies the algorithms used by detecting module 164.

Computing device 106 may also include additional components that, for clarity, are not shown in FIG. 2. For example, computing device 106 may include a power supply to provide power to the components of computing device 106. Similarly, the components of computing device 106 shown in FIG. 2 may not be necessary in every example of computing device 106.

Signal quality is a key factor in developing machine learning methods for detection, tracking, and prediction of specific event based on time-series data. Low quality signals may impact the performance both at the training phase (E.g. resulting in a classifier that is influenced by noise) as well as during test and operation phase where the results may become less reliable. Therefore, it is crucial to remove low quality signals in both phases. Throughout the rest of this document, we use signals representing breathing and activity as an example, but the methods presented can be applied to any other signals of a repetitive nature, such as industrial processes. Each of the industrial processes described in the background can be modeled as a repetitive process; each process includes a nominally correct operation that can be used as a reference model when checking subsequent operations. The quality of each operation can be improved through the use of a suite of sensors and through the use of artificial intelligence to detect deviations from a reference model of operation.

In one example approach, one can develop a reference model from the time-series data of the sensor devices and then leverage that reference model when checking subsequent operations. In one such example approach, semi-supervised learning (i.e., expert labeling of a supposedly successful operation) may be used to detect and reject outliers in the process. In another such example approach, outlier rejection is used in the step-wise concatenation of failures to eliminate failures. For instance, step-wise concatenated filtering of failures may be used to:

1) filter out failures due to insufficient injected material (i.e., operator-aborted molding or smelting runs);
2) filter out failures due to a machine being out-of-spec (i.e., a robot dropped a bolt, a robot failed to acquire an image, or the mold injector failed to reach nominal pressure); and
3) filter out failures due to quality fails on final product (i.e., the car failed a dimensional measurement or the smelted ore failed a density test).

In one example approach, the signals received from sensors 104 may include measurement samples used to detect, track, or predict a specific event, such as symptoms or conditions related to some aspect of a user. Such signals may, however, be degraded due to, for instance, placement of the sensor 104, sensor degradation, interference with the step of measuring the signal, or noise in the signal. The wearable device may, therefore, fail to capture or may only partially capture the actual breath breathed by the subject. Such events may happen, for instance, when the wearable device is not worn properly and thus has a poor contact with the body or when the wearable device is worn but the subject is performing a physical activity affecting the quality of the measured breath.

To address this, in some example approaches, a signal processing module 162 acts to improve the quality of the signals, or to reduce the effect of using lower quality samples of the signals. In one such example approach, signal processing module 162 searches for usable measurement samples in the sensor data. In one example approach, signal processing module 162 receives sensor data associated with a sensor 104 that monitors a biological function, the sensor data representing time-series measurement samples of one or more parameters associated with the biological function being monitored by the sensor 104. The sensor data includes usable and unusable samples of the time-series measurements. Signal processing module 162 extracts data representing two or more features of samples of the time-series measurements and then filters the extracted data by eliminating outliers in the extracted data based on an expected outlier ratio. In one example approach, signal processing module 162 then trains a machine learning algorithm to identify usable samples of the sensor data based on the filtered extracted data.

Figure 3:
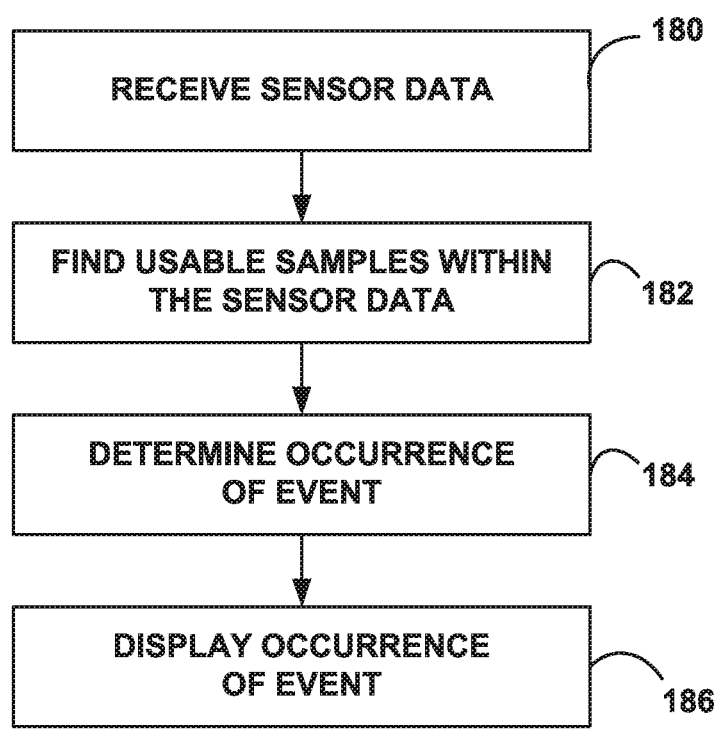
FIG. 3 is a flow diagram illustrating an example technique for detecting and displaying an event representative of an aspect of a biological function, in accordance with one aspect of the disclosure.

FIG. 3 is a flow diagram illustrating an example technique for detecting and displaying an event representative of an aspect of a biological function, in accordance with one aspect of the disclosure. In the example approach of FIG. 3, signal processing module 162 receives sensor data (180) and finds usable measurement samples in the sensor data (182). Signal processing module 162 then analyzes the usable samples to determine when an event has occurred (184). User interface 108 receives notice that an event has occurred and displays information relevant to the event when the event occurs (186).

Lightweight and wearable physiological monitors may monitor and record a variety of health and wellness conditions. Such monitors may be used by, for instance, detecting module 164 to detect parameters relevant to a user. In some examples, machine learning is used to determine relevant parameters of the biological function and to calculate weights to be associated with such parameters when determining the occurrence of a relevant event, or the detection of a specific state, trigger or trend. In some such examples, detecting module 164 receives sensor data from a plurality of users and clusters the users based on the sensor data.

Figure 4A:
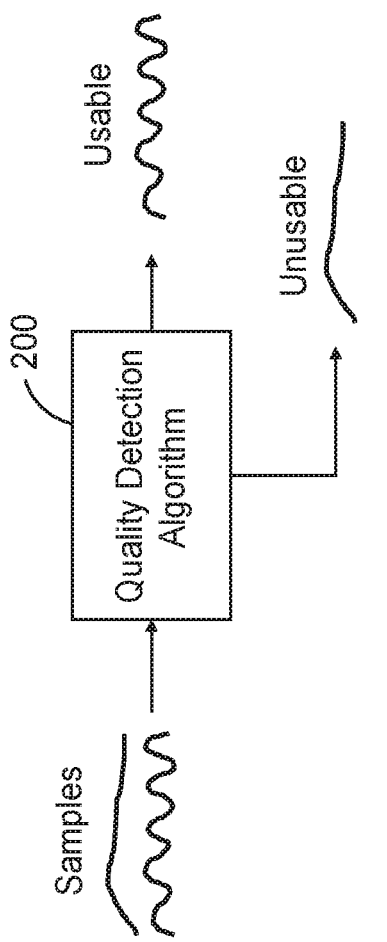
FIGS. 4A and 4B illustrate quality detection algorithms, in accordance with one aspect of the disclosure.
Figure 4B:
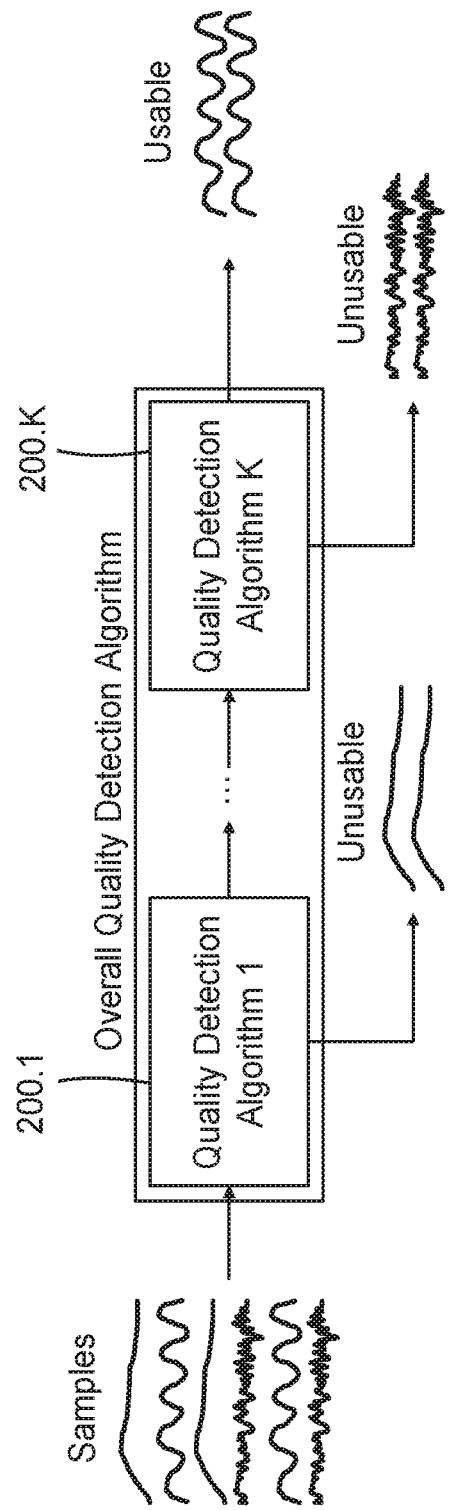

In one example approach, signal processing module 162 includes a quality detection algorithm. FIGS. 4A and 4B illustrate quality detection algorithms, in accordance with one aspect of the disclosure. In the example approach of FIG. 4A, quality detection algorithm 200 may be used to determine if a sample is of acceptable quality or not. Once quality detection algorithm 200 is trained, it can be used as shown in FIG. 4A to detect quality samples from measurement samples received from sensor 104.

In some example approaches, an overall quality detection algorithm 202 includes two or more quality detection algorithms 200.1-200.$k$, each tuned to filter out unusable samples. In one such example approach, overall quality detection algorithm 202 applies the individual quality detection algorithms 200.1-200.$k$ in series to achieve higher overall performance in filtering out unusable samples from the measurement samples. As an example, the first quality detection algorithm 200.1 may perform as the simplest pre-filter, rejecting only the most obvious instances of unusable measurement samples. Each successive algorithm 200 refines the filter by selecting for gradually more subtle features which are characteristics of a usable measurement sample.

Figure 5:
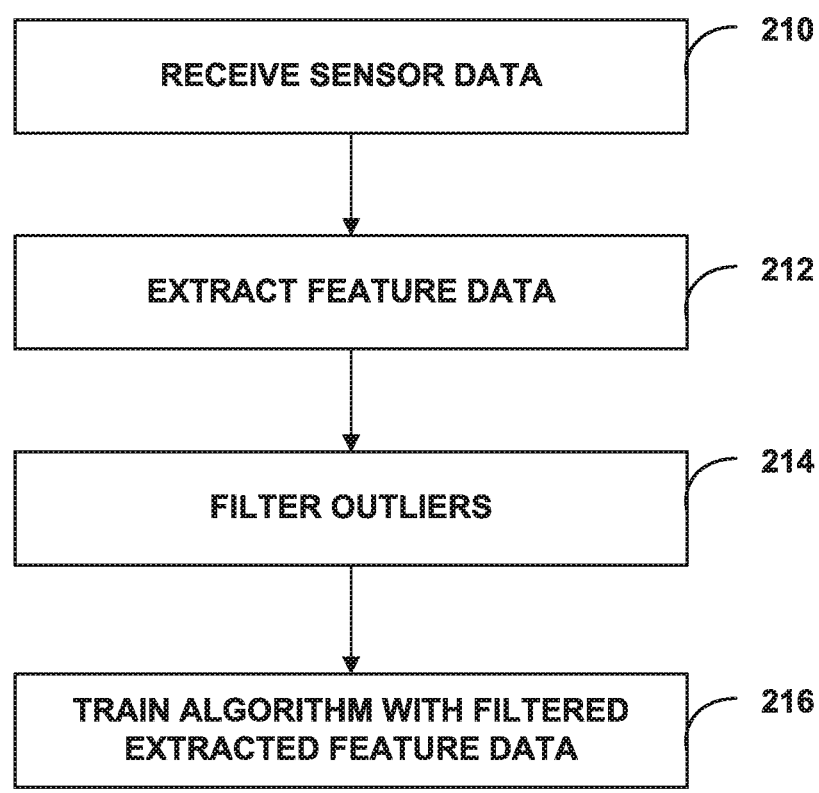
FIG. 5 is a flow diagram illustrating an example technique for training one or more quality detection algorithms, in accordance with one aspect of the disclosure.

FIG. 5 is a flow diagram illustrating an example technique for training one or more quality detection algorithms, in accordance with one aspect of the disclosure. In the example approach of FIG. 5, sensor data is received (210) and feature data is extracted from the sensor data (212). Outliers within the extracted feature data are filtered from the extracted data (214). The remaining extracted data is used to train one or more quality detection algorithms 200.K (216).

One approach for detecting usable measurement samples would be to "label" a set of time-series measurement samples as usable or unusable, leveraging domain knowledge via either visual inspection or by using a reference measurement. For example, the reference measurement samples can be obtained from a different source.

In one example approach, the biological function being monitored is breathing. In one such example approach, a usable breath is a measured breath that represents an actual breath breathed by the subject wearing sensor 104. In some such example approaches, a usable breath is one that it is not colored by environmental or motion artifacts and that has sufficient signal-to-noise ratio. At the same time, a usable time interval is a time interval that contains two or more usable breaths. In some example approaches, detecting module 164 uses one or more algorithms 200.1-200.$k$ to determine if a time interval includes a usable breath. In some example approaches, detecting module 164 uses one or more algorithms 200.1-200.$k$ to determine if one of the two or more breaths detected in a given time interval include a usable breath.

In one example breathing measurement approach, breathing measurement samples are collected via a pressure sensor that senses abdominal movement while a ventilation mask with flow sensors is used to collect reference breathing samples used as labeled data to train one or more quality detection algorithms 200. In another example approach, domain knowledge and the visual inspection by an expert of the raw data captured by sensor 104 are used to determine usable breath vs unusable breath. The samples noted as usable are labeled as such. One may use the labeled data to train one or more quality detection algorithms 200. In one such example approach, training module 166 uses the labeled data to train signal processing module 162 to detect and discard unusable samples.

In one example approach, one may use the labeled data, extract features, and train machine learning classification algorithms using techniques such as random forest, gradient boosting, and neural networks. This approach will result in one or more quality detection algorithms 200.

Figure 6:
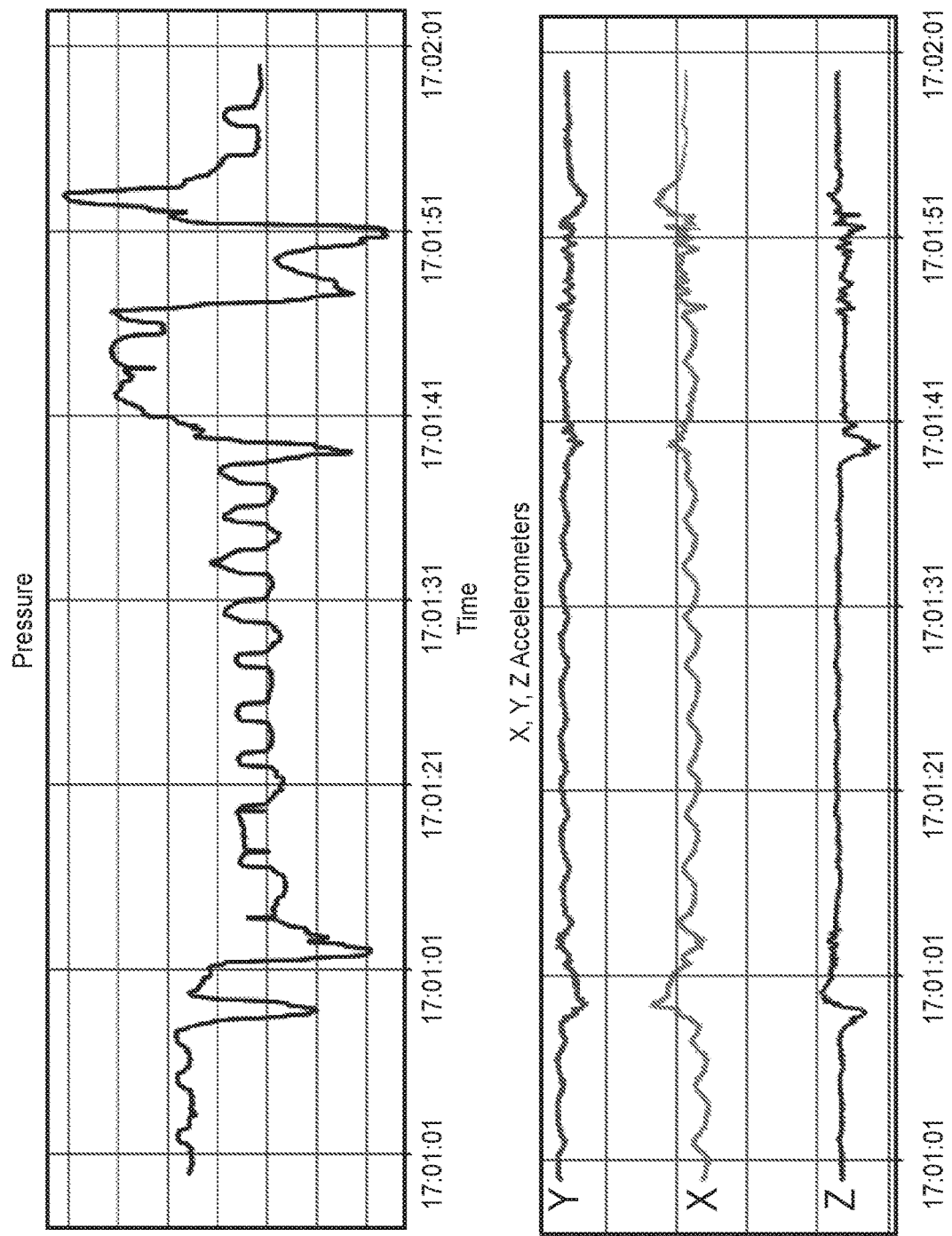
FIG. 6 illustrates measurements of user breathing, in accordance with one aspect of the disclosure.

In one example breath monitoring system, a pressure sensor and three accelerometers are used to measure samples taken of the breathing patterns of user 102. FIG. 6 illustrates measurements of user breathing, in accordance with one aspect of the disclosure. Note that the signal shapes are just notional and may also contain not only one sensor signal but multiple signals per sample. For example, one sample may include data from a pressure sensor stacked with accelerometer data from x, y, and z axes. FIG. 6 shows sample signals that includes sample pressure data and x, y, z, accelerometer data.

In one example approach, features are extracted from each sample to be used later in the pipeline. For instance, features such as the number of peaks, value of the peaks, inhalation time, and exhalation time may be extracted from breath samples. In one such approach, features associated with breathing samples may be extracted from each individual sensor signal such as pressure, x, y, and z, or from the combination of the signals by applying cross spectral density or other methods.

In one example approach, one may use domain knowledge in both the feature extraction and training phases. For example, if high frequency noise is expected, one may use this information and include features based on higher frequency components of the samples to be used for algorithm development. In one such example approach, machine learning classification methods such as random forest, gradient boosting, and neural networks are used to develop a breath quality detection algorithm. Quality detection algorithm 200 is the output of the training process. Generated algorithm 200 may be used to determine the quality of unseen data and classify the data into the categories of usable vs unusable breath. The required features and feature calculation pipelines are also embedded into the algorithm k block.

At times, it can be difficult to acquire the desired labeled data. It can be very time consuming to obtain labeled data as, as noted above, the production of labeled data requires inspection by an expert of individual samples or the generation of reference signals used to compare to the samples being measured. In the absence of labeled data, one may approximate labeled data by carefully controlling the environment in which samples are taken.

Figure 7:
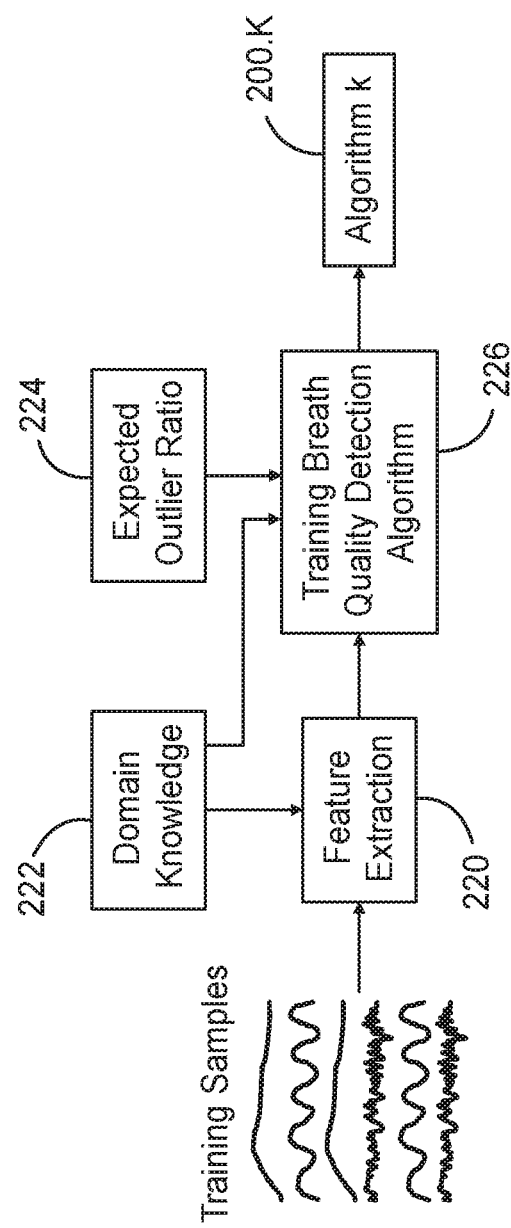
FIG. 7 is a flow diagram illustrating another example technique for training one or more quality detection algorithms, in accordance with one aspect of the disclosure.

FIG. 7 is a flow diagram illustrating another example technique for training one or more quality detection algorithms, in accordance with one aspect of the disclosure. In the example approach of FIG. 7, user 102 is asked to wear user device 101 and to perform a certain activity. For example, user 102 may be asked to sit for a period of time or to read a book for a period of time. As seen in FIG. 7, time-series sensor data is received from sensor 104. Data representing two or more features of samples of the time-series measurements are extracted at feature extraction 220. In some example approaches, domain knowledge 222 determines the features to extract at feature extraction 220.

Depending on the activity, a certain percentage of the samples will tend to be usable and the rest will tend to be unusable (outliers). An expected outlier ratio 224 is used to select the most likely usable samples based on their extracted features and selected extracted features are then used to train machine learning algorithms such as quality detection algorithms 200.$k$ at training breath quality detection algorithm 226 based on one-class classification techniques that distinguish usable samples from unusable samples as a function of domain knowledge 222 and the expected outlier ratio 224. In some example approaches, training module 166 uses machine learning one-class classification methods such as isolation forest and One-Class Support Vector Machine (SVM) to develop one or more breath quality detection algorithms 200.

In one example approach, the expected outlier ratio is set based on the task performed by the users 102. For example, the expected outlier ratio for sitting may be lower than the expected outlier ratio for walking at a slow pace. In one example approach, training module 166 asks user 102 for feedback regarding the specific activity. Other sensor data such as accelerometer, gyroscope, global navigation satellite system, or camera footage may be used in addition to determine the activity type and the desired expected outlier ratio.

In one example approach, features may be extracted from breath samples to be used later in the pipeline shown in FIG. 7. These features may include number of peaks, value of the peaks, inhalation time, exhalation time, etc. Features may be extracted from each individual sensor signal such as pressure, x, y, and z, or from the combination of the signals by applying cross spectral density or other methods.

The approach shown in FIG. 7 may be used to train user devices 101 for new users 102. In one example approach, each new user 102 is guided through a prescribed series of activities designed to generate and isolate model breathing samples for algorithm generation. In one example approach, user 102 is asked to perform a physical exercise, followed by a calmer period of relaxation. The user is then asked to start a timer at the beginning of the relaxation phase such that sensor 104 can capture a sequence of deeper breaths progressing toward a condition of steady state calm.

In another example approach, users 102 are prompted by a metronome generating a slow rhythmic pattern and asked to synchronize their breathing over a period of 5 minutes, during which time the sensor 104 collects breathing patterns. In one such example approach, the frequency of the provided metronome is compared to the principal frequency of the breathing signal as a metric for quality. In one example approach, the user is asked to experiment with different sensor positions until an optimal or acceptable signal to noise ratio is achieved. In one such example approach, training exercises are programmed into an initial and interactive set of activities for all new users, so that a usable breath detection algorithm may be tuned for each individual user.

Figure 8:
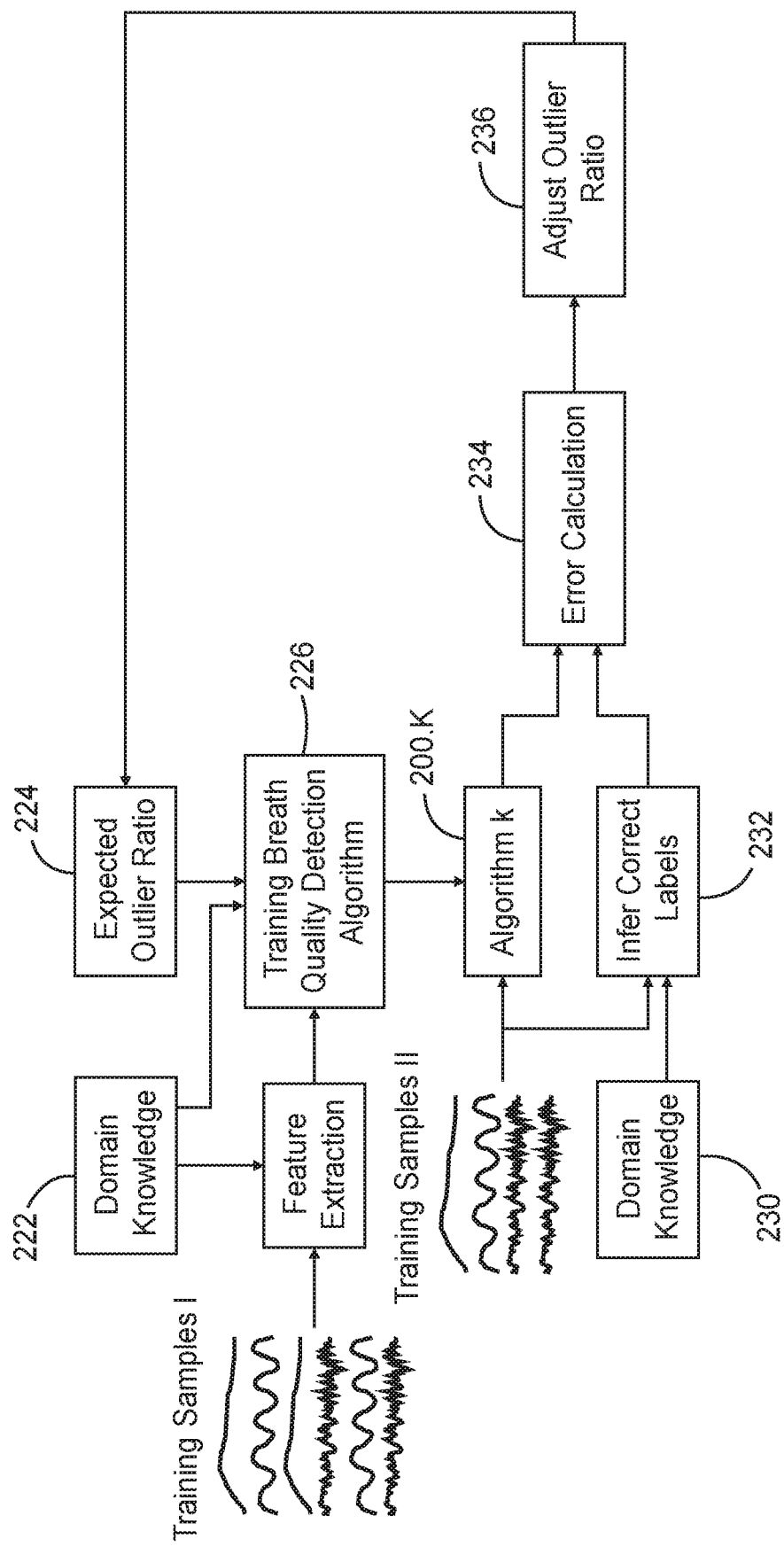
FIG. 8 is a flow diagram illustrating yet another example technique for training one or more quality detection algorithms, in accordance with one aspect of the disclosure.

FIG. 8 is a flow diagram illustrating another example technique for training one or more quality detection algorithms, in accordance with one aspect of the disclosure. In the example approach shown in FIG. 8, a first set of training samples are used to develop an algorithm 200.K via feature extraction 220, domain knowledge 222, expected outlier ratio 224 and training breath quality detection algorithm 226 in the approach described in the context of FIG. 7 above. In the example approach shown in FIG. 8, a second set of training samples, labeled at a labeler 232 based on domain knowledge 230, is compared to labels assigned via algorithm 200.K. In this example approach, the labels generated at labeler 232 are treated as the truth, while the labels generated by algorithm 200.K are checked for deviations from the truth. An error calculated by error calculator 234 as a function of the comparison of the labels assigned by algorithm 200.K and the labels generated based on domain knowledge 230 is used to adjust the expected outlier ratio at adjust outlier ratio 236. The expected outlier ratio then becomes a mechanism for tuning one or more algorithms 200 based on a comparison of labeled data (the "ground truth") to labels generated by algorithms 200. In some example approaches, the check at 234 is for one or more of false positives and true negatives.

The revised outlier ratio is then used with the first set of training samples to adjust algorithm 200.K to reduce the error generated as a function of the comparison between the labels generated by algorithm 200.K and the labels inferred at labeler 232. An advantage of the approach shown in FIG. 8 is that even a small set of labeled data can be leveraged at algorithm 200.k and labeler 230 to achieve better performance. This process can repeat as often as needed to ensure the quality detection algorithms 200.K capture the most recent changes in the signals measured by sensor 104.

A number of techniques may be used for quality detection. In the following discussion, the examples are based on a user device 101 that is monitoring the breathing of user 102. The techniques may be applied, however, to other time-series measurement samples.

A common source of zero- or low-quality breath sample is when a subject is not wearing device 101 at all or if the subject is wearing device 101 but is performing some vigorous physical activity such as running Therefore, one can develop a quality detection algorithm by detecting these two cases and identifying any breath samples within one of these conditions as outlier.

Figure 9:
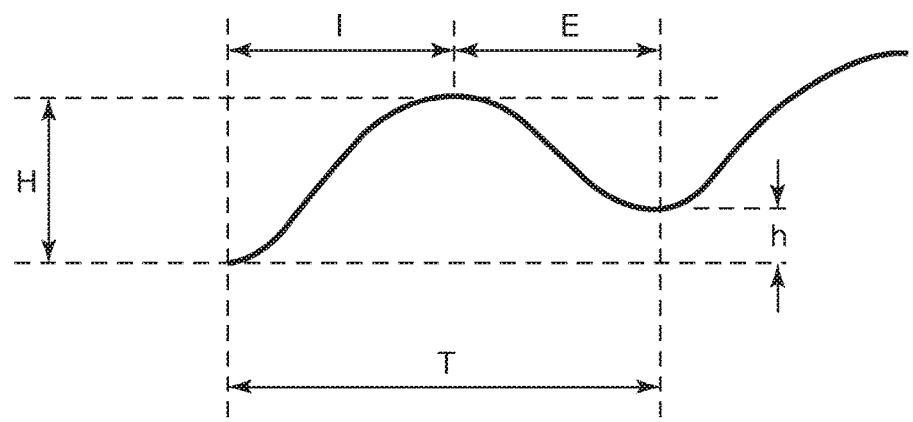
FIG. 9 illustrates features representative of breath samples, in accordance with one aspect of the disclosure.

As noted above, in some example approaches, features of a breath sample are extracted from the breath sample and the techniques discussed above are used to generate a breath quality detection algorithm 200.K. FIG. 9 illustrates features representative of breath samples, in accordance with one aspect of the disclosure. As shown in FIG. 9, these features include features such as relative amplitude (H), duration (T), volume (area under the curve), slope (h/T), inhalation time (I), exhalation time (E) or inhalation/exhalation ratio (UE). Representative usable and unusable breath samples are shown in FIG. 10.

Figure 10:
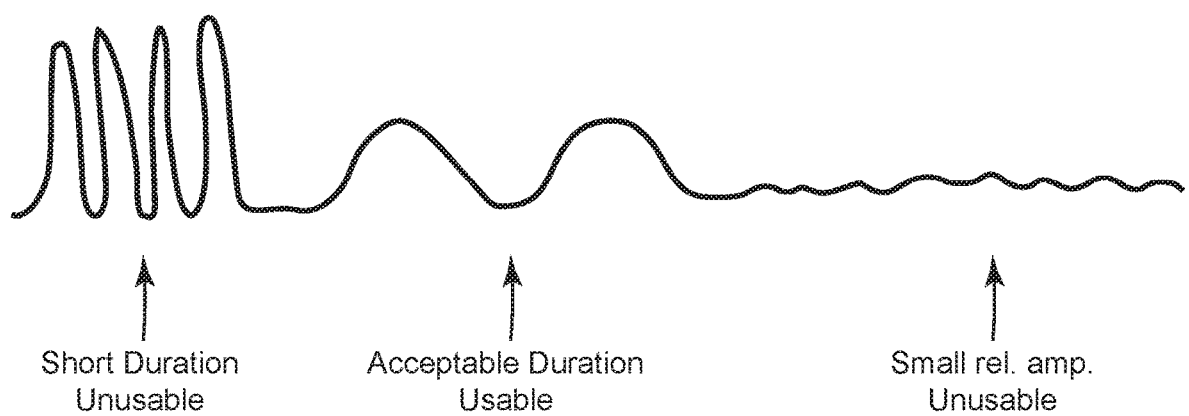
FIG. 10 illustrates representative usable and unusable breath samples, in accordance with one aspect of the disclosure.

In one example approach, an algorithm which has been trained using any of the labeling approaches discussed above may be used to identify normal or physically reasonable ranges for each of the breath parameters listed above or illustrated in FIGS. 9 and 10. A simple breath quality detection algorithm may, for instance, reject any breath, or any breathing time period, in which the breath parameters exceed the reasonable range.

Figure 11:
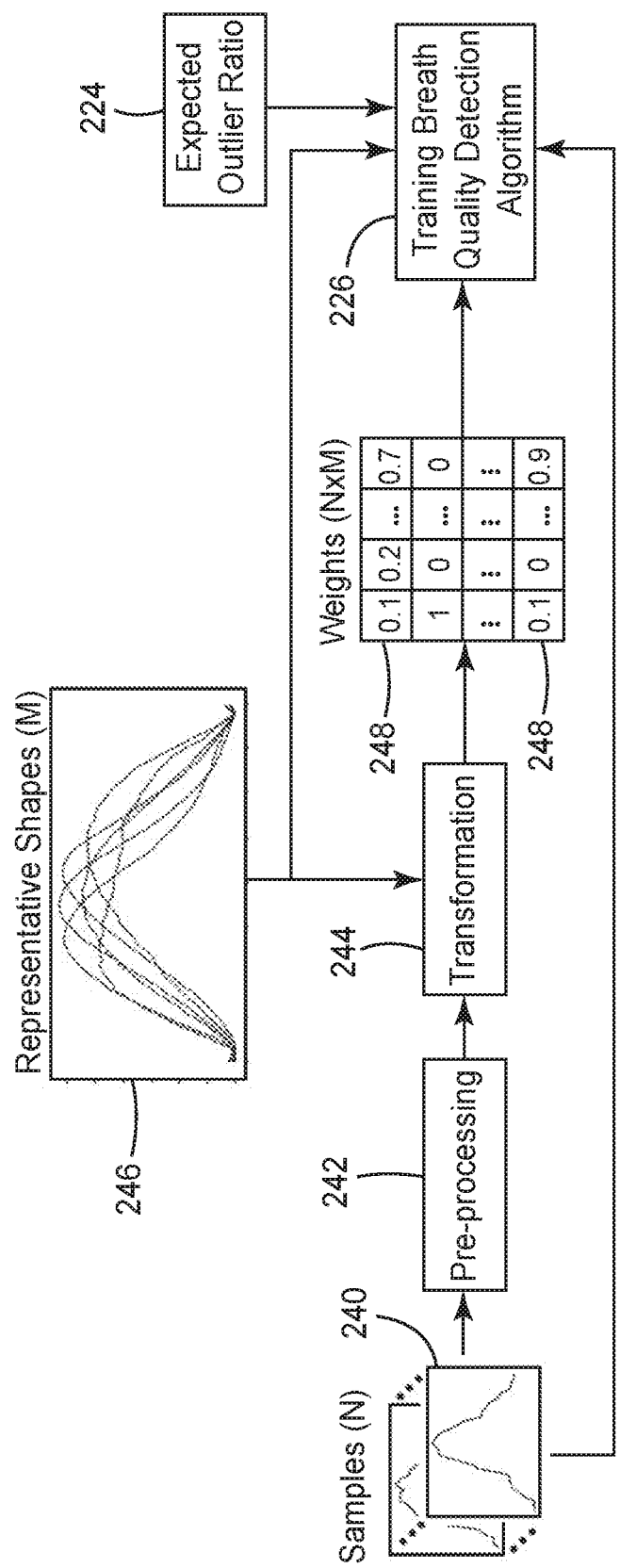
FIG. 11 illustrates a technique for determining the quality of the samples based on the morphology of the samples, in accordance with one aspect of the disclosure.

It is possible to leverage the morphology of samples to determine the quality of the samples. FIG. 11 illustrates a technique for determining the quality of the samples based on the morphology of the samples, in accordance with one aspect of the disclosure. In one example approach, shapes extracted from measurement samples 240 are compared to representative shapes 246 and one or more representative shapes 246 are selected as representative of the extracted shapes.

In some such example approaches, samples 240 are pre-processed at 242 before passing to transformation block 244. In some such example approaches, pre-processor 242 normalizes the breath in time and amplitude to ensure all pre-processed samples have the same relative amplitude and duration.

In one example approach, samples are transformed at transformation block 244. In one such example approach, pre-processed samples are transformed as a function of the representative shapes. The samples are transformed into another space based on the representative shapes, where each sample is represented by a vector. In one implementation, the shape that has the least error compared with a sample shape may be selected. In other implementations, a sample shape may be represented by a weighted sum of multiple representative shapes by using various optimization techniques with appropriate regularization. In such an implementation, the weights are the result of the transformation process and result in an N×M matrix 248. Element (i, j) of this matrix, shows the degree by which sample i can be represented by representative shape j.

In one example approach, representative shapes 246 may be obtained using different methods. For instance, one may use domain knowledge to generate representative model shapes or heuristic shapes. In another approach, one may use actual samples to extract representative shapes through methods such as dictionary learning.

Figure 12:
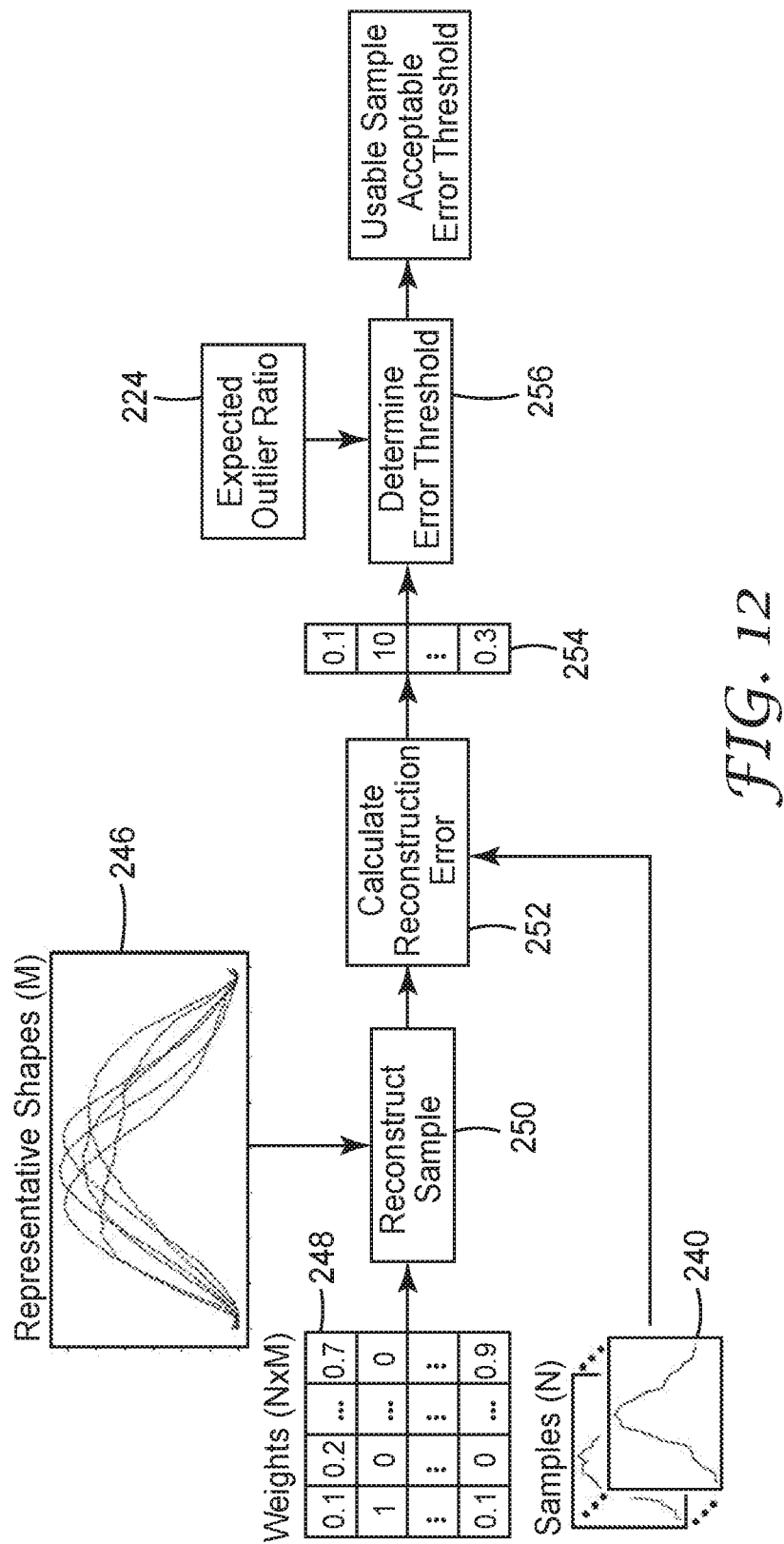
FIG. 12 illustrates a technique for determining the quality of time-based measurement samples, in accordance with one aspect of the disclosure.

FIG. 12 illustrates another technique for determining the quality of time-based measurement samples, in accordance with one aspect of the disclosure. In the example approach of FIG. 12, training module 166 reconstructs, at 250, a sample breath as a function of the representative shapes 246 and the weights 248 by applying the equation:

$$X\hat{} = W*D$$

where $X\hat{}$ is an N×L matrix of N reconstructed samples with length of L, W is the weight matrix, and D is the representative shapes matrix of size M×L. Training module 166 calculates a reconstruction error, at 252, as, for example, the mean absolute error, mean squared error, or root mean squared error between the actual samples and the reconstructed samples. In one such example approach:

$$E = \text{sqrt}(X - X\hat{})*\alpha$$

where sqrt applies element wise square function, X is the original samples matrix, $X\hat{}$ is the reconstructed samples matrix, and α is a weight matrix 254 of shape N×1. One example for α is an N×1 matrix with all elements set to 1. Using artificial intelligence classification techniques, or expert domain knowledge, a threshold for acceptable errors can then be established and applied as a breath quality detection algorithm.

In one example approach, training module 166 establishes a threshold for acceptable errors at 256 using the expected outlier ratio 224 and either artificial intelligence classification techniques or expert domain knowledge. The threshold may then be applied as a breath quality detection algorithm.

Figure 13:
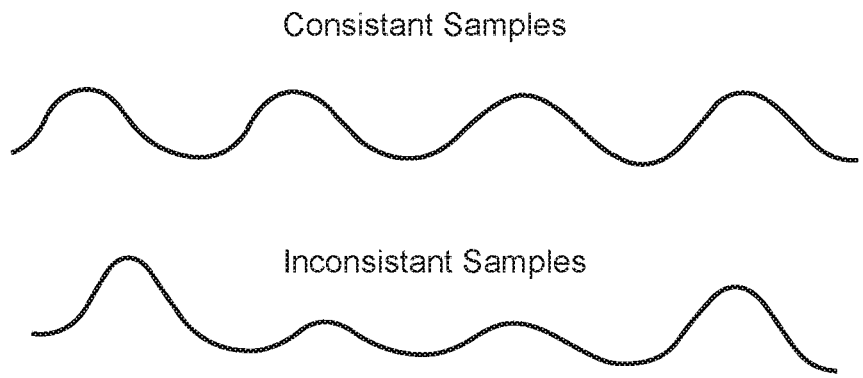
FIG. 13 illustrates another technique for determining the quality of time-based measurement samples, in accordance with one aspect of the disclosure.

FIG. 13 illustrates another technique for determining the quality of time-based measurement samples, in accordance with one aspect of the disclosure. The consistency of samples may be a strong indicator of the usability of sensor data. In the example of FIG. 13, hypothetical samples are shown from a wearable device 101 that captures measurement samples representing the breathing of user 102.

As can be seen in FIG. 13, the upper samples 260 show a consistent height, shape, and periodicity over the time interval. However, the lower samples 262 are not consistent in amplitude. This might happen due to intermediate repositioning of the wearable device 101. In general, usable samples should be consistent over at least a minimum interval of time. One may use one of the approaches described above to generate a quality detection algorithm 200.K to verify the consistency of the breath. In this case, samples need to be processed in batches as the goal is to determine the consistency over several samples. In some example approaches, methods such as robust covariance estimation, auto-correlation, or other one-class classification methods are used. In some example approaches, the size of the cluster may also indicate the quality of the set. For example, if the robust covariance of a set is close to zero, it means that the samples in the interval all have similar features and are thus "similar" to each other.

One objective of quality detection algorithms 200 is to determine the quality of samples within a data set. In one example approach, only samples with sufficiently high quality are used to develop models for detection, tracking, and prediction of specific events. This may be referred to as hard outlier rejection (where the low-quality samples are completely ignored).

In another implementation, the quality scores of the samples in the data set are used as a weighting factor for determining quality detection algorithms. In some such implementations, samples with lower quality are treated as less "important" during the development phase when compared to samples of higher quality. Such an approach may, for instance, be referred to as soft outlier rejection as it will not completely ignore low-quality samples, but reduce their impact based on their quality score.

Figure 14:
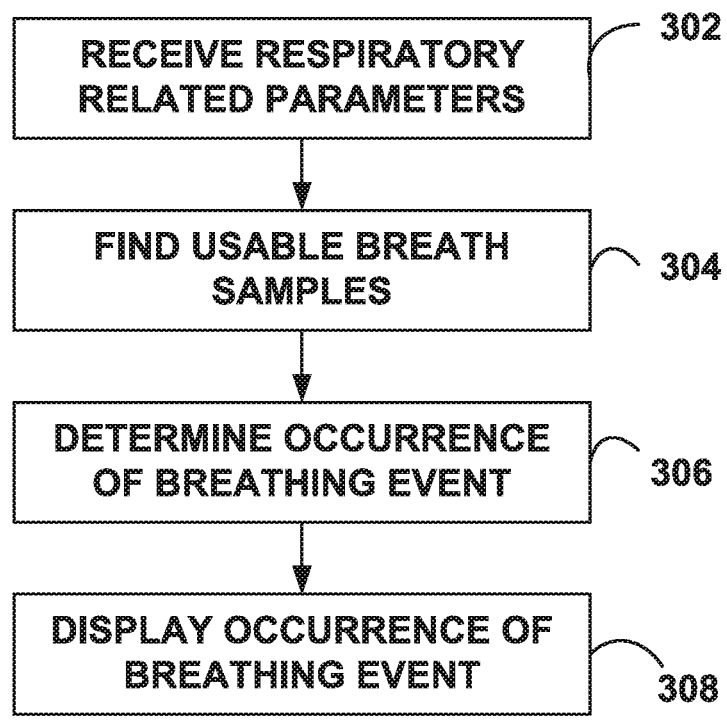
FIG. 14 illustrates a flow diagram of an example technique for notifying a user of an occurrence of a breathing event.

FIG. 14 illustrates a flow diagram of an example technique for notifying a user of an occurrence of a breathing event. Although the technique of FIG. 14 will be described with respect to respiratory monitoring system 100 of FIG. 1 and computing device 106 of FIG. 2, in other examples, the technique of FIG. 14 may be performed using a different system, a different computing device, or both. Additionally, respiratory monitoring system 100 and computing device 106 may perform other techniques for notifying a user of an occurrence of a breathing event.

The technique illustrated in FIG. 14 includes receiving, by computing device 106, at least one output representative of at least one respiratory related parameter (302). Respiratory related parameters include respiratory parameters, environmental information, location information, user information, and the like. In some examples, respiratory parameters include amplitudes, rates, and durations of inhalation, exhalation, or both. In other examples, respiratory parameters may include other parameters indicative of respiration, such as ventilation flow rate, tidal volumes, consistency of respiration rate, pulse rate, oxygen-saturation, acoustic spectral density, and the like. In some examples, sensor 104 generates at least one output representative of the at least one respiratory related parameter. In other examples, computing device 106 receives the at least one output representative of the at least one respiratory related parameter from other sources, such as, for example, user interface 108, a third-party computing device, or the like.

After receiving the at least one output representative of the at least one respiratory related parameter, the technique illustrated in FIG. 14 includes finding usable breath samples via one or more of the quality detection algorithms 200 described above (304). The technique then determines an occurrence of a breathing event based on the at least one usable breathing sample (306). In an asthma monitoring application, a breathing event may, for instance, include detecting a smooth breathing state (e.g., improved breathing relative to average ventilation), detecting a hard-breathing state (e.g., worse breathing relative to average ventilation), or the like. In some examples, determining the occurrence of the breathing event based on the at least one output includes comparing the at least one output representative of the at least one respiratory related parameter to a respective baseline respiratory related parameter. For example, where the output representative of the at least one respiratory related parameter includes an amplitude and frequency (e.g., an average rate of a repeated respiratory parameter) of respiration of user 102, the respective baseline respiratory related parameter may include an average amplitude and frequency of respiration of user 102. Additionally, or alternatively, the respective baseline respiratory related parameter may include an average amplitude and frequency of respiration of an average person with similar or substantially the same physical characteristics as user 102 (e.g., age, gender, height, weight, medical conditions, or the like). In other examples, other respiratory related parameters, such as duration of inhalation or amplitude, frequency, or duration of exhalation, may be compared to a respective baseline respiratory related parameter.

In other examples, one or more different approaches may be used to determine a baseline respiratory related parameter. In one example approach, user 102 may rest for a specified time interval (e.g., 5 minutes), during which sensor 104 measures and determines a set of average baseline respiratory parameters (e.g., normal breathing. In another example approach, computing device 106 selects a time period near the beginning of each day and gathers information from sensor 104 to establish baseline respiratory parameters for the respective day. In another example approach, computing device 106 stores a histogram of respiratory parameters collected over a period of several days to several weeks. In this approach, a baseline respiratory parameter may be defined as any parameter that falls within one standard deviation of the average over several days or weeks. In another example approach, the computing device 106 gathers statistical information. In one such approach, baseline respiratory parameters may be based on one or more characteristics of one or more sub-groups of users. For instance, one may define a baseline as a respiratory parameter which is typical of patients within a certain nursing home, or which is typical for users who have been prescribed on a new respiratory medication for more than two weeks, or which is typical for residents of a city when the weather conditions exceed certain limiting values of, for instance, temperature or humidity or air quality levels, or the like.

In some examples, the baseline respiratory related parameters may be stored by computing device 106. In other examples, the baseline respiratory related parameters may be stored by a third-party computing device, or the like. The baseline respiratory related parameters may be initially determined based on user input. For example, initial baseline respiratory related parameters may be based on preexisting baseline respiratory related parameters determined for person having a similar age, gender, height, weight, medical conditions, or the like compared to user 102. In this way, computing device 106 may be configured to determine baseline respiratory parameters that are personalized to user 102.

In some examples, the baseline respiratory parameters are fixed. In other examples, the baseline respiratory parameters vary over time. For example, computing device 106 may adjust (e.g., modify or update) one or more baseline respiratory parameters at regular or irregular intervals, in response to user input, determined occurrences of breathing events, or the like. By adjusting the baseline respiratory parameters, computing device 106 may improve the accuracy of the baseline respiratory parameters, assist user 102 in changing the average respiration of user 102 over time, or the like.

In some examples, comparing the at least one output representative of the at least one respiratory related parameter to a respective baseline respiratory related parameter includes determining whether the at least one output representative of the at least one respiratory related parameter is within a respective threshold value of the respective baseline respiratory related parameter. In some examples, the respective threshold values may be fixed. For example, the respective threshold values may be predetermined based on user input. In other examples, the respective threshold values may vary over time. For example, in response to user input, computing device 106 may adjust (e.g., modify or update) one or more baseline respiratory parameters at regular or irregular intervals, in response to user input, determined occurrences of breathing events, data received from modules 162, 164 or 166, or the like. In some examples, the determination of a breathing event may depend on contextual information. For example, the threshold value used to determine a breathing event may be adjusted according to one or more of a location of user 102 (e.g., whether user 102 is indoors or outdoors), environmental information (e.g., whether the user has been exposed to unusual environmental factors, such as extreme weather or air quality issues), activity of user 102 (e.g., whether the user is physically active or at rest), and breath event history (e.g., whether the user has reported other respiratory symptoms within the past 24 hours).

After determining the occurrence of a breathing event, the technique illustrated in FIG. 14 includes displaying, on display 210 of user interface 208, an indication of the occurrence of the breathing event (308). For example, as discussed above, computing device 106 includes output devices 156. Output devices 156 provide video output via user interface 108 to display 170. Additionally, or alternatively, output devices 156 may provide other output media to a user, such as tactile output, audio output, or the like. By providing output media to user interface 108, computing device 106 may notify user 102 of an occurrence of a breathing event. In other examples, computing device 106 may utilize communications units 154 to communicate the indication of the occurrence of the breathing event with one or more external devices via network 110. By communicating the indication of the occurrence of the breathing event with one or more external devices, computing device 106 may notify user 102 of an occurrence of a breathing event by the one or more external devices.

In some examples, machine learning is used to determine relevant respiratory related parameters and to calculate weights to be associated with such respiratory related parameters when determining the occurrence of a breathing event, or the detection of a breathing state, trigger or trend. In some such examples, detecting module 164 receives potential respiratory related factors collected from a plurality of users. Some of the users exhibit what is classified as normal breathing, while others exhibit breathing patterns associated with certain breathing disorders. By comparing the respiratory related parameter information to a dictionary of respiratory related parameters, derived, for instance, from both normal and asthmatic people, detecting module 164 may calculate, for each user, a breathing score which correlates to the severity of their asthma symptoms. In addition, detecting module 164 may determine, for each user, respiratory related parameters most relevant to determining their breathing state.

Lightweight and wearable physiological monitors may monitor and record a variety of health and wellness conditions. Such monitors may be used by, for instance, detecting module 164 to detect parameters relevant to determining a respiratory function of a user. For instance, detecting module 164 may be used to detect the severity of and to monitor breathing disorders such as asthma and chronic obstructive pulmonary disease (COPD). Monitoring methods may include detection of chemical elements from exhaled breath, acoustic sounds (cough or wheeze) detected at the chest or throat, and measurements of the relative motion in the chest wall or abdomen. In one example approach, sensor 104 includes a device that measures respiration based on the pressure exerted between the chest or abdomen and a piece of clothing, such as a belt or elastic band, as described in more detail below. In one such example approach, the device measures respiratory related parameters such as the cycle time of a respiratory cycle, and one or more of the tidal volume, inspiratory flow, inspiratory pause, expiratory flow and expiratory pause for each person being measured.

Figure 15:
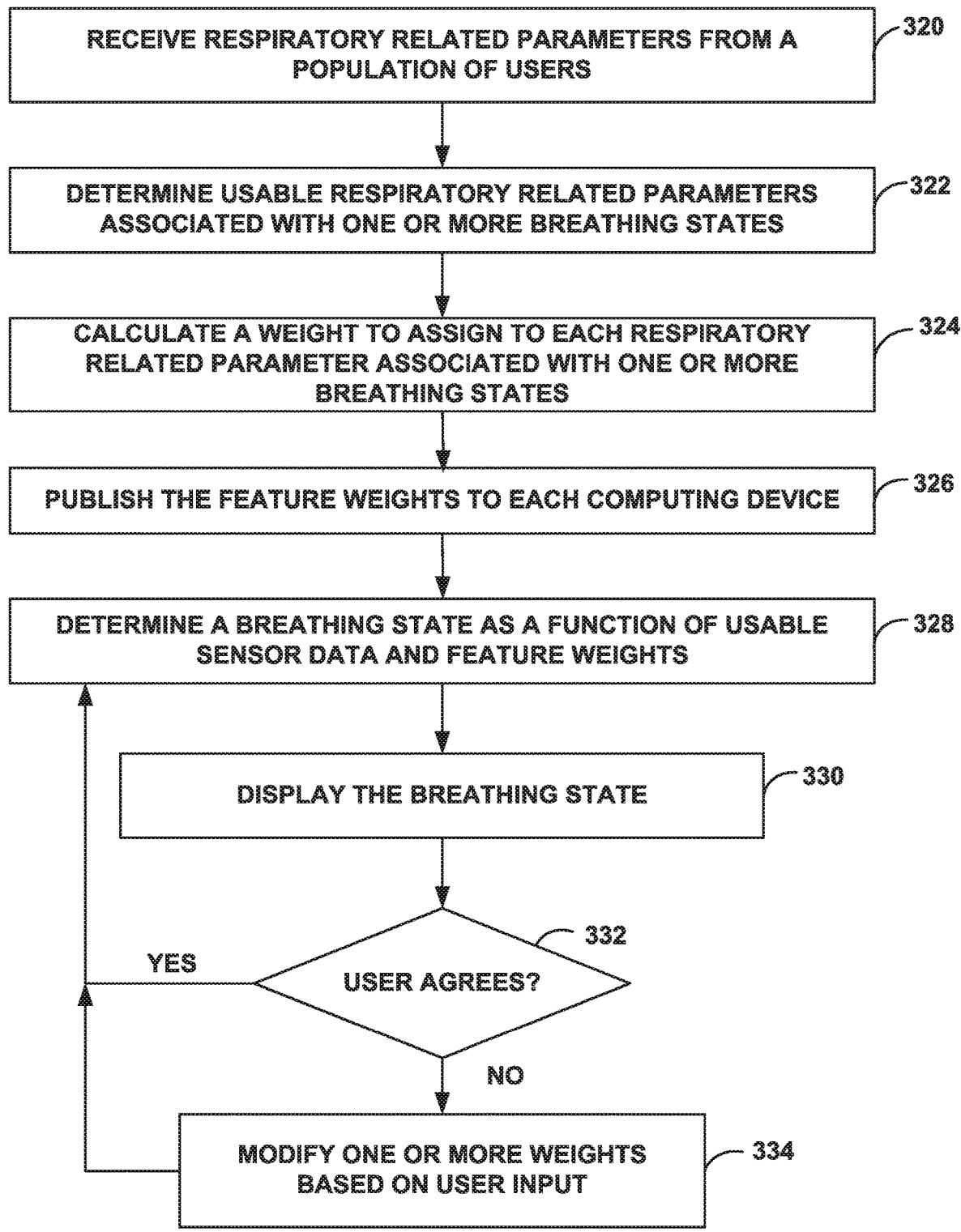
FIG. 15 is a flow diagram of an example technique for detecting a condition such as a breathing state of a user.

FIG. 15 is a flow diagram of an example technique for detecting a condition such as a breathing state of a user. Although the technique of FIG. 15 will be described with respect to system 100 of FIG. 1, in other examples, the technique of FIG. 15 may be performed using a different system, a different computing device, or both. Additionally, system 100 and computing device 106 may perform other techniques for receiving respiratory related parameters.

In one example approach, the technique illustrated in FIG. 15 includes receiving potential respiratory related parameters collected from a population of users (320). In an example based on the detection and monitoring of asthma, the population of users includes people with and without asthma. The asthma condition is characterized by physiologists as an airway obstruction, usually caused by bronchial inflammation. Asthma is described as a reversible airway obstruction in that certain drugs, such as the beta agonist albuterol, can partially reverse the condition and allow for temporary relief in the asthma subject.

In one example approach, detecting module 164 determines usable respiratory related parameters that help distinguish between an asthmatic breathing state and a normal breathing state, and that help distinguish asthmatic breathing states from other common conditions such as rapid breathing due to physical exercise or excitement (322). A variety of techniques for detecting usable samples are described above.

In one example approach, detecting module 164 seeks to detect signs of airway obstruction. Detecting module 164 then assigns weights to the respiratory related parameters deemed most relevant in determining a given condition (such as a breathing state, breathing event, trigger or trend) (324) and stores an indication of the relevant parameters in a feature vector. Detecting module 164 then publishes the weights associated with each feature in the feature vector for that condition to computing devices 106 (326).

In one example approach, computing device 106 receives the weights associated with each feature in a feature vector and applies the weights to respiration related parameters received at the computing device 106 to determine if a condition has been met (328). For instance, a feature vector associated with detection of labored asthmatic breathing may include features associated with respiration related parameters received from sensor 104 and features associated with respiration related parameters receive as environmental information. As one example, a feature vector is a string of coded words. Each word in the string represents a respiratory related parameter, a weight assigned to a respiratory parameter, or the like. In this way, the feature vector provides an efficient approach to summarize, store in memory, or both all, or nearly all, of the respiratory related parameters used by computing device 106 (or detecting module 164) to detect, determine, or evaluate a breathing state.

In one example approach, when a condition is met, the user is notified via user interface 108 (330). In one such example approach, the user may indicate whether he or she agrees with the determination (332). If the user agrees with the determination (YES branch), computing device 106 continues to monitor respiration related parameters at 328. If, however, the user does not agree with the determination (NO branch), computing device 106 modifies one or more weights of features in the feature vector to reflect the feedback received from the user (334) before returning to monitor respiration related parameters at 328.

In one example approach, as noted above, detecting module 164 determines both the feature vector and the weights used, at least initially, by computing devices 106. For example, detecting module 164 may classify the severity of asthma from breathing patterns recorded from a pressure sensor on a user's abdomen. In one example approach, detecting module 164 applies a preprocessing algorithm to reject breathing patterns with low Signal-to-Noise-Ratio (SNR) and then applies a feature extraction method to develop a feature vector for each condition based on relevant respiration related parameters. Detecting module 164 then determines, for instance, whether the breathing features collected across a population of users may be used, for example, to classify the severity of the asthma symptoms of each patient.

A representative preprocessing algorithm is discussed next. Since, in the example above, the breathing signal coming from a pressure sensor is a continuous signal, in one example approach, different instances of breathing are first segmented and synchronized with each other. This may involve, for instance, detecting a beginning time-point and the ending time-point of each breath.

The time duration of each breath may then be calculated and stored as one of the features representing the breath signal. In one example approach, when synchronizing the breathing signals, the duration time of each breathing signal is scaled such that each time-scaled breathing signal lasts the same amount of time. To keep the same number of samples in the breathing signals, in one example approach, the time-scaled signals are resampled to have same number of samples.

A method of feature extraction will be discussed next. In one example approach, detecting module 164 uses respiration related parameters such as physiological parameters, environmental parameters, user information and measured sensor 104 data received from the preprocessing step above to train one or more classification algorithms. In one such example approach, detecting module 164 uses a labeled set of breathing features received from a population of subjects to train each classification algorithm.

For instance, in one example approach, detecting module 164 uses a labeled set of aggregated breathing features to train a classification algorithm to predict the severity of asthma symptoms. In one such approach, detecting module 164 receives a labeled set of breathing features gathered over time. For instance, such a labeled training set may be generated by presenting a questionnaire about severity of asthma symptoms to the subjects of an experimental study, every 8 hours, while monitoring each subject's breathing. The questionnaire responses are then transformed to represent asthma symptoms severity as a scalar value. Detecting module 164 then applies a classification algorithm such as logistic regression or decision tree to estimate the likelihood that the respiratory related parameters associated with the features in the feature vector can be used to distinguish severe asthma symptoms from healthy or normal breathing. If successful, detecting module 164 may isolate a scalar value representative of asthma severity, or "asthma severity score," and be able to use this asthma severity score as feedback to the wearer of the sensor 104.

In another example approach, storage components 158 stores a generalized feature vector, with un-weighted respiratory related parameters pending refinement based upon user input. In one such approach training module 166 refines the feature vector based upon a labeled set of breathing features gathered over time. For instance, such a labeled training set may be generated by presenting a questionnaire about severity of asthma symptoms to each new user, every 8 hours, while monitoring the user's breathing. The questionnaire responses are then transformed to represent asthma symptoms severity as a scalar value. In one such example approach, computing device 106 applies a classification algorithm such as logistic regression or decision tree to estimate the likelihood that the respiratory related parameters associated with the features in the feature vector can be used to distinguish severe asthma symptoms from healthy or normal breathing.

In one some example approach, users 102 monitor variations in the asthma severity scores generated by computing device 106 over a period of several days to several weeks. Such an approach may then be used by the user to track variations in environmental influences or in the management of their disease, with a sensitivity and consistency difficult to derive from their own self-diagnosis.

In one example approach, detecting module 164 discards from the aggregated feature vector, features that have minimal impact on the asthma severity score, or whose impact falls below a selected threshold. Detecting module 164 then assigns weights representing the contribution of each feature in the aggregated feature vector to the severity score and distributes the aggregated feature vector and its associated weights to each computing device 106.

In one example approach, detecting module 164 uses a quantization method similar to Voronoi-tessellation to reduce the dimensionality of the feature vector. In this method, a k-means clustering algorithm with "L" number of clusters assigns a cluster index to each feature vector. Each feature vector may, therefore, be represented as an integer scalar number (with a value between 1 and L).

Returning to the example of the asthma severity score discussed above, since there is a natural variation in breathing signal instances, a decision regarding the severity of asthma symptoms should be made based on observed variation in breathing signal patterns during a long period of time (i.e., over an hour or several hours). To represent the variation in the measured breathing signals in this period of time, in one example approach, detecting module 164 employs a histogram of the quantized breathing patterns to represent the change in patterns over time. Such a histogram may represent, for example, the frequency of the occurrence of different breathing patterns during that period of time and may be represented as an L-dimensional vector termed an aggregated feature vector. Other lossy and lossless compression techniques may also be used to collect the requisite respiration related parameters over time. In such an approach, detecting module 164 uses a labeled set of aggregated breathing features to train a classification algorithm to predict the severity of asthma symptoms. As above, detecting module 164 may receive a labeled set of aggregated breathing features gathered over time. Detecting module 164 then applies a classification algorithm such as logistic regression or decision tree to estimate the likelihood that the aggregated feature vector represents severe asthma symptoms versus a healthy or normal breathing. If successful, detecting module 164 may isolate a scalar value representative of the asthma severity score, and be able to use this asthma severity score as feedback to the wearer of the sensor 104.

In some examples, one or more functions of detecting module 164, as discussed above with respect to FIG. 15, may be performed by computing device 106. For example, computing device 106 may receive from detecting module 164 an un-weighted feature vector. After receiving the un-weighted feature vector, computing device 106 may receiving user input during a training period (e.g., computing device 106 may gather information from survey questions from the user over one or more days). After receiving user input, computing device 106 may determine (e.g., calculate) an initial set of weights for use in the detection algorithm. After determining an initial set of weights, computing device 106 may receive subsequent user input and incrementally adjust the weights based on the subsequent user input. In this way, computing device 106 may be configured to adjust the classification algorithm.

In some examples, displaying the occurrence of the breathing event (330) includes communicating a notification to user 102 via a display 170 of the user interface 108. Output device 156 may provide video output to display 170 via user interface 108. Additionally, or alternatively, output device 156 may provide other media output (e.g., tactile output, audio output, or the like) to user interface 108 or other external devices. The notification includes an indication of at least one of a breathing state, an occurrence of a breathing event, a trigger associated with at least one occurrence of a breathing event, a trend associated with at least one occurrence of a breathing or at least one trigger, and advice associate with a breathing state, at least one occurrence of a breathing event, at least one trigger, at least one trend, or the like.

In some examples, computing device 106 queries a location information module to determine location information that is temporally associated with, for example, the occurrence of a breathing event before transmitting such information to a user via display 170 of user interface 108. For example, computing device 106 may direct processor 150 to store a present location of user 102 in location information module. The location information module may then communicate the location information to at least one of storage components 158.

In some example approaches, computing device 106 may determine whether a breathing event has occurred based on a location that is associated with sedentary activity of user 102, such as an abode or place of work of user 102, or dynamic activity of user 102, such as a gym or when user 102 is moving. As another example, computing device 106 may determine whether a breathing event has occurred based on a location that is associated with one or more occurrences of breathing events, such as a location having an allergen to which user 102 is sensitive. By basing the algorithm on location information, respiratory monitoring system 100 may more accurately determine at least one of an occurrence of a breathing event, a trigger associated with at least one occurrence of a breathing event, a trend associated with at least one occurrence of a breathing or at least one trigger, advice associate with at least one occurrence of a breathing event, at least one trigger, at least one trend, or the like.

In some examples, an environmental information module uses the location information to determine one or more environmental parameters temporally associated, spatially associated, or both with the occurrence of the breathing event. For example, in response to determining an occurrence of a breathing event, computing device 106 may cause an environmental information module to determine, from an environmental information platform, one or more environmental parameters based on the present location of user 102. In other examples, the environmental information module may determine one or more environmental parameters based on user input, estimated spatial information associated with user 102 (e.g., a last known location of user 102, the location of an abode or place of work of user 102, or the like), or the like. The environmental information module may communicate one or more environmental parameters to at least one of storage components 158.

Computing device 106 may determine whether a breathing event has occurred based on one or more environmental parameters. For example, computing device 106 may determine the algorithm based on one or more of temperature, barometric pressure, percent humidity, dew point, percent chance of precipitation, percent cloud cover, wind speed, air quality index (e.g., value, category, or both), dominant pollutants, pollen counts (e.g., relative ratings associated with different types of pollen, or the like), UV index, like environmental parameters, or expected values of such environmental parameters or trends of values of such environmental parameters. As one example, detection may be based on an air quality index of a present or predicted location of user 102, such that computing device 106 generates a notification to user 102 indicating a probability of an occurrence of a breathing event. By basing detection of a breathing event on one or more environmental parameters, respiratory monitoring system 100 may more accurately determine at least one of an occurrence of a breathing event, a trigger associated with at least one occurrence of a breathing event, a trend associated with at least one occurrence of a breathing or at least one trigger, advice associate with at least one occurrence of a breathing event, at least one trigger, at least one trend, or the like.

In some examples, detecting module 164 uses at least one of an occurrence of a breath event, a location of user 102, and one or more environmental parameters to determine a trigger associated with a respective occurrence of a breathing event. A trigger is associated with an occurrence of a breathing event when the trigger is related to the occurrence of one or more breathing events (e.g., temporal concurrence or spatial correlation), causes the occurrence of one or more breathing events (e.g., a contributing factor, an originating factor, or an exclusive factor), or the like. In some examples, a trigger includes a potential trigger. A potential trigger may be based on at least one of location information, one or more environmental parameters, or user input before the occurrence of a breathing event. In one example approach, a trigger module may communicate the occurrence of the breathing event to at least one of storage components 158.

In some examples, a determination that a particular location is associated with an occurrence of a breathing event may be based on two or more breathing events occurring in the particular location, on user input (e.g., the user identifies a location as more likely than not to be associated with an occurrence of a breathing event), or the like. As one example, the trigger module may determine that a particular outdoor area is a trigger when the particular outdoor area is associated with two or more hard breathing events.

In the same or different examples, a determination that one or more environmental parameters are associated with an occurrence of a breathing event may be based on two or more breathing events occurring when the one or more environmental parameters occur in proximity to user 102. For example, the trigger module may determine that a particular air quality index is a trigger when two or more breathing events occur in a location having an air quality index equal to or greater than a particular air quality index value (air quality indices range from 0, most good, to 500, most hazardous).

In some example approaches, computing device 106 may notify a user 102 based on one or more triggers. As one example, notification may be based on a trigger associated with a particular location or one or more environmental parameters, such that the notification is based on a probability of an occurrence of a breathing event in the particular location, when the one or more environmental parameters are present, or both. By basing the notification on one or more triggers, monitoring system 100 may more accurately determine at least one of an occurrence of a breathing event, a second trigger associated with at least one occurrence of a breathing event, a trend associated with at least one occurrence of a breathing or at least one trigger, advice associate with at least one occurrence of a breathing event, at least one trigger, at least one trend, or the like.

In some examples, detecting module 164 uses two or more occurrences of a breathing event, a location of user 102, one or more environmental parameters, and one or more triggers to determine a trend associated with a respective occurrence of a breathing event. A trend identifies a plurality of occurrences of breathing events that are associated with one or more locations, one or more environmental parameters, user input, or the like, as discussed above. For example, detecting module 164 may determine a notification that indicates one or more locations, one or more environmental parameters, user input, or the like that are associated with a plurality of occurrences of breathing events. Detecting module 164 may communicate a trend to at least one of storage components 248. By determining and communicating trends, monitoring system 100 may notify user 102 of triggers.

In some examples, detecting module 164 uses a trend to determine one or more potential occurrences of breathing events, potential triggers, or the like. As one example, detecting module 164 may determine that a particular location is associated with an occurrence of a breathing event, and computing device 106 may generate a notification to user 102 when user 102 is near, approaching, or in the particular location. As another example, detecting module 164 may determine that one or more environmental parameters are associated with an occurrence of a breathing event, and computing device 106 may generate a notification to user 102 when the one or more environmental parameters are present at the location of user 102, when environmental information shows a trending toward the one or more environmental parameters, or the like. As another example, detecting module 164 may determine that past user input is associated with an occurrence of a breathing event, and computing device 106 may generate a notification to user 102 when user 102 provides the same or similar current user input to computing device 106. By determining a trend, monitoring system 100 may notify user 102 of a potential occurrence of a breathing event before a breathing event occurs. In this way, detecting module 164 may determine a notification that indicates a potential occurrence of a breathing event.

Computing device 106 may also generate a notification to user 102 identifying occurrences of breathing events over a period of time, ranking triggers (e.g., locations, one or more environmental parameters, user input, or the like), indicate a probability of a future occurrence of a breathing event, or the like. By basing notification on one or more trends, respiratory monitoring system 100 may more accurately determine at least one of an occurrence of a breathing event, a trigger associated with at least one occurrence of a breathing event, advice associate with at least one occurrence of a breathing event, at least one trigger, at least one trend, or the like.

In some examples, detecting module 164 uses at least one of an occurrence of a breath event, a location of user 102, one or more environmental parameters, one or more triggers, and one or more trends to determine advice. Advice may include any suitable information to assist user 102 in improving the respiratory function of user 102. For example, detecting module 164 may determine a notification that indicates one or more locations, one or more environmental parameters, user input, one or more triggers, or the like are associated with occurrences of one or more breathing event. Detecting module 164 may communicate advice to at least one of storage components 158. By determining and communicating advice, monitoring system 100 can notify user 102 of advice.

Figure 16:
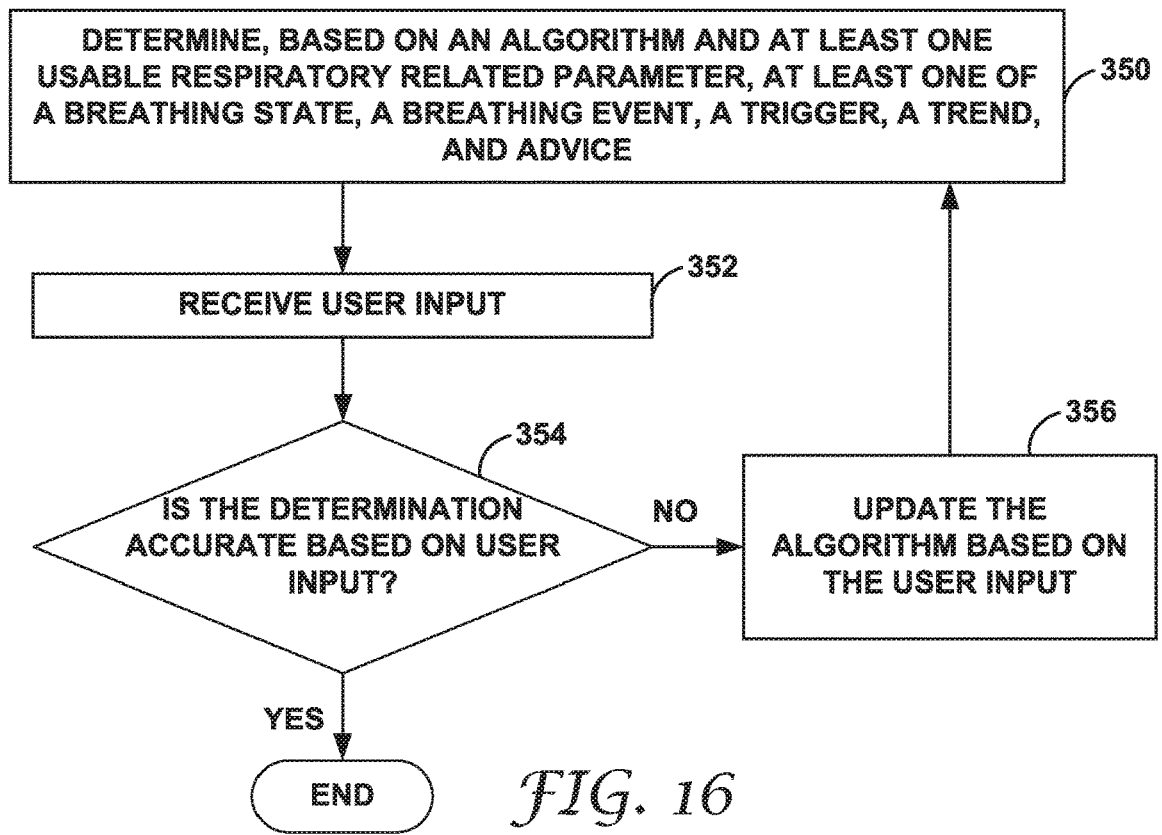
FIG. 16 is a flow diagram of an example technique for adjusting a detection algorithm based on input from a user, in accordance with one aspect of the disclosure.

In some examples, computing device 106 may adjust (e.g., modify or update) detection of breathing events, trends and other indicators of respiratory function based on input from user 102. FIG. 16 is a flow diagram of an example technique for adjusting a detection algorithm based on input from a user 102, in accordance with one aspect of the disclosure. Although the technique of FIG. 16 will be described with respect to system 100 of FIG. 1 and computing device 106 of FIG. 2, in other examples, the technique of FIG. 16 may be performed using a different system, a different computing device, or both. Additionally, system 100 and computing device 106 may perform other techniques for receiving respiratory related parameters.

The technique illustrated in FIG. 16 includes, determining, by computing device 106, for example, at least one a trigger, a trend, and advice based on at least one of the occurrence of a breathing event, environmental information, location information, and a user input (350). For example, computing device 106 may apply a method to determine (e.g., a first algorithm) at least one a trigger, a trend, and advice based on at least one of the occurrence of a breathing event, environmental information, location information, and a user input.

After determining at least one a trigger, a trend, and advice (350), the technique of FIG. 7 includes receiving an input from user 102 (352). The user input is associated with at least one of the determined trigger, determined trend, and determined advice.

After receiving the user input at 352, the technique of FIG. 16 includes determining whether the determined trigger, determined trend, and determined advice is accurate based on the received user input (354). For example, the received user input may include an indication that at least one of a location and one or more environmental parameters was associated with an occurrence of a breathing event. In some examples, the second user input may indicate that the determined trigger, determined trend, and determined advice is accurate (YES branch). In other examples, the received user input may indicate that the determined trigger, determined trend, and determined advice is inaccurate (NO branch). In this way, the technique of FIG. 16 includes determining whether or not the first algorithm is accurate. In examples in which the algorithm is accurate (YES branch), the algorithm may not be adjusted, and the technique may end.

In examples in which the algorithm is inaccurate (NO branch), computing device 106 may adjust the first algorithm based on the second user input to generate a second algorithm (356). After generating the second algorithm at 356, the technique illustrated in FIG. 16 includes, again determining, by computing device 106, for example, at least one a trigger, a trend, and advice based on at least one of the occurrence of a breathing event, environmental information, location information, and a user input (repeating step 350). Computing device 106 may repeat steps 350, 354, and 356 n-times until the nth algorithm is accurate. By adjusting the algorithm based on the received user input, respiratory monitoring system 100 may more accurately determine at least one of an occurrence of a breathing event, a trigger associated with at least one occurrence of a breathing event, a trend associated with at least one occurrence of a breathing or at least one trigger, advice associate with at least one occurrence of a breathing event, at least one trigger, at least one trend, or the like.

Figure 17:
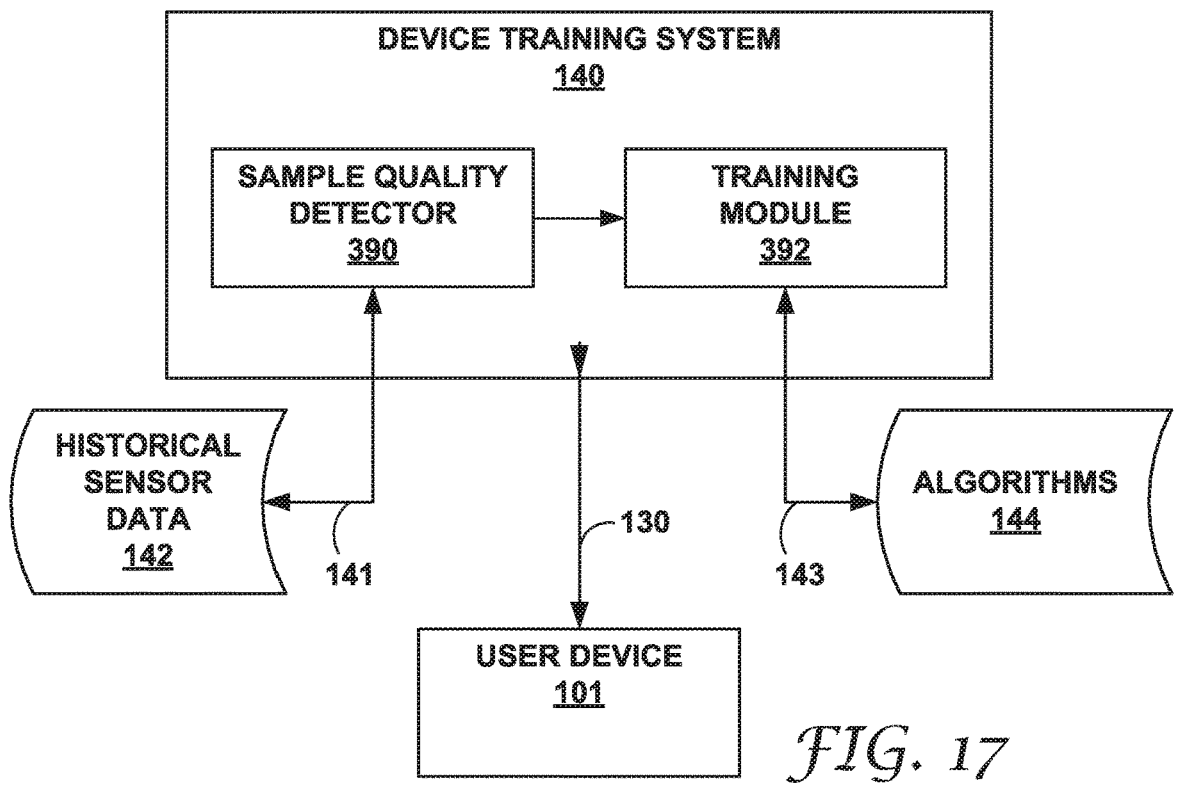
FIG. 17 is a block diagram illustrating a device training system, in accordance with one aspect of the disclosure.

FIG. 17 is a block diagram illustrating a device training system, in accordance with one aspect of the disclosure. In the example shown in FIG. 17, device training system 140 includes a sample quality detector 390 and a training module 392. Sample quality detector 390 is connected to historical sensor data 142 via link 141. Training module 392 is connected to algorithm storage 144 via link 143. In some example approaches, device training system 140 is connected via a link 130 to a user device 101. In one example approach, device training system 140 includes a computing device, one or more storage components and a user interface.

Figure 18:
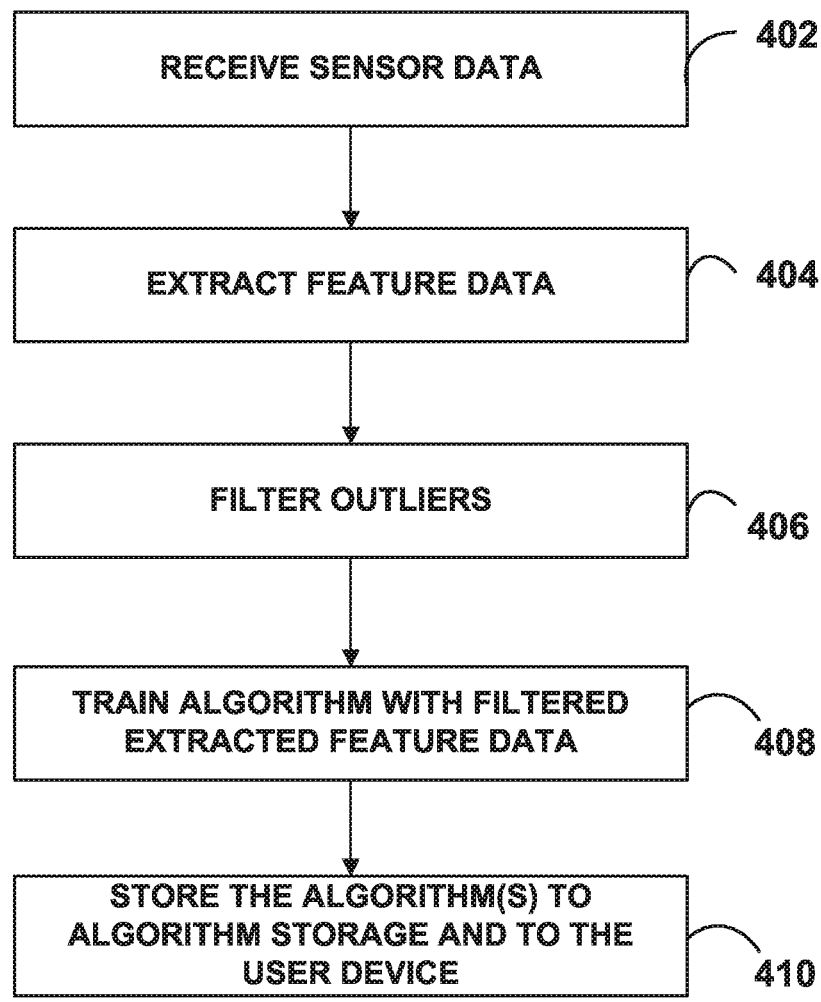
FIG. 18 illustrates a flow diagram of an example technique for generating an algorithm used to detect quality samples, in accordance with one aspect of the disclosure.

FIG. 18 illustrates a flow diagram of an example technique for generating an algorithm used to detect quality samples, in accordance with one aspect of the disclosure. Although the technique of FIG. 18 will be described with respect to respiratory monitoring system 100 of FIG. 1, in other examples, the technique of FIG. 14 may be performed using a different system, a different computing device, or both. Additionally, respiratory monitoring system 100 may perform other techniques for generating an algorithm used to detect quality sample.

The technique illustrated in FIG. 18 includes receiving at least one output representative of at least one respiratory related parameter (402) from historical sensor data 142. Respiratory related parameters include respiratory parameters, environmental information, location information, user information, and the like. In some examples, respiratory parameters include amplitudes, rates, and durations of inhalation, exhalation, or both. In other examples, respiratory parameters may include other parameters indicative of respiration, such as ventilation flow rate, tidal volumes, consistency of respiration rate, pulse rate, oxygen-saturation, acoustic spectral density, and the like. In some examples, device training system 140 receives the at least one output representative of the at least one respiratory related parameter from other sources, such as, for example, computing device 106, a third-party computing device, or the like.

After receiving the at least one output representative of the at least one respiratory related parameter, the technique illustrated in FIG. 18 includes extracting feature data from the historical data (404) and filtering outliers in such feature data (406). The technique then determines one or more quality detection algorithms 200 based on the at least one usable breathing sample (408) before storing the algorithms 200 to one or more of algorithm storage 144 and user device 101.

Techniques for detecting events based on time-series measurement samples of one or more parameters associated with the biological function being monitored by the sensor device will be described next.

Figure 19:
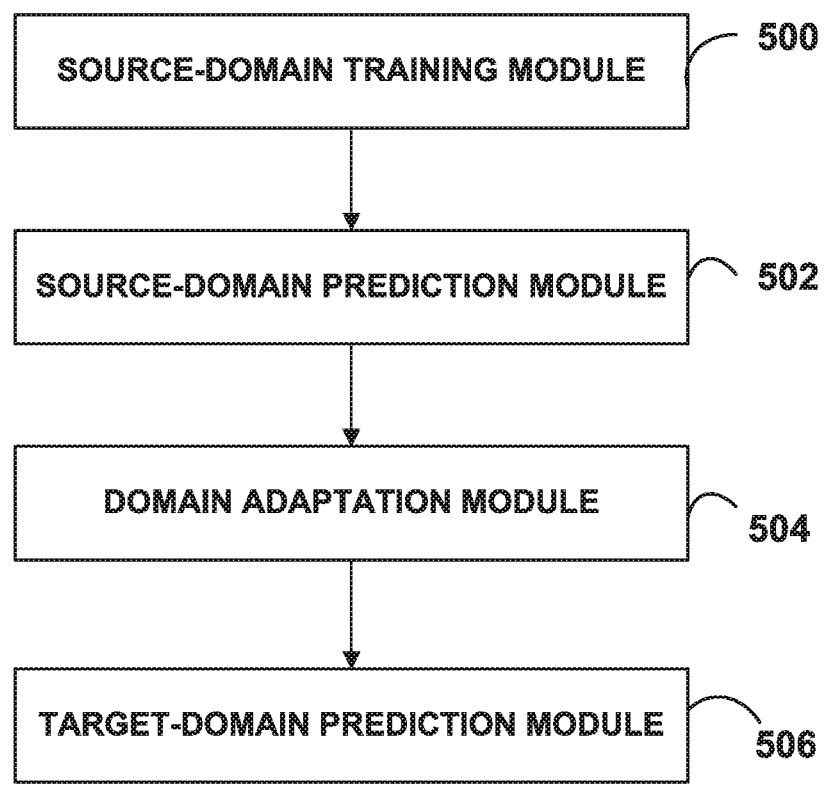
FIG. 19 illustrates a technique for adding new users to a monitoring system, in accordance with one aspect of the disclosure.

FIG. 19 illustrates a technique for adding new users to a monitoring system, in accordance with one aspect of the disclosure. In one example approach, the technique leverages historical data from a set of wearable devices alongside with data received from the new user to detect, track, and predict events. The technique, which is based on the idea of transfer learning, enables speedy onboarding of new users (technically known as the "target" users) by leveraging classifiers that are accurately trained by the data available for existing users (technically known as "source" users) of the device.

In the context of transfer learning, the main challenge is that the distribution of the data acquired from the wearable device can be drastically different across users. This may be caused due to different wearing habits of users or biological dissimilarities among them. Therefore, mere application of a classifier trained on the data acquired from one participant to another may yield no better results than a random classifier. In the transfer learning literature, the concept of "negative learning" is built to describe the scenarios where the data distribution between the users is so different that transferring classifiers may even harm the classification outcome.

While the technique is described in terms of wearable sensors and users of such devices, it can be applied to other domains and other type of sensors where sensor characteristics are not identical. Throughout the rest of this document, we use signals representing breathing and activity as an example, but the methods presented can be applied to other signals of cyclic nature.

In one example approach, the technique of FIG. 19 applies a pipeline including a source-domain training module 500, a source-domain prediction module 502, a domain adaptation module 504, and a target-domain prediction module 506. In one such example approach, the source-domain training module 500 uses the data from various existing source-users to train accurate classifiers. The source-domain prediction module 502 applies the classifiers trained by module 500 to unlabeled data samples (collected from target users' devices) and makes predictions for them. The domain adaptation module 504 leverages the (perhaps very few number of) labeled and unlabeled samples that are acquired from target-domain users to adjust the existing source-domain classifiers to the (potentially-different) distribution of data from new users. Finally, the target-domain prediction module 506 aggregates the predictions from modules 502 and 504 to boost the prediction accuracy of one or more of modules 502 and 504. In the figures of this section, the boxes with dashed lines contain the (classification or clustering) rules that are experimentally learned from the data. Solid line boxes represent, for instance, datasets.

In one example for the monitoring of breath patterns, A source domain prediction model may be derived from the historical data of a large number of clinical subjects in a breathing study, while a target domain model may be sought with characteristics of a particular individual or with characteristics particular to a class of individuals, e.g. the group of people who are diagnosed with asthma.

In another example, using the example of home HVAC systems, a set of time-series data can be used to monitor the functionality of installed air filters for different HVAC units. In this case, the source-domain comprises the units from which plenty of labeled time-series data is collected and the target domain includes any new HVAC unit that might be unseen in the source domain. Similar to the diversity that exist between human users in the previous biological example, the HVAC units can be very different depending on their size, age, manufacturer, environmental conditions, and installation.

Figure 20A:
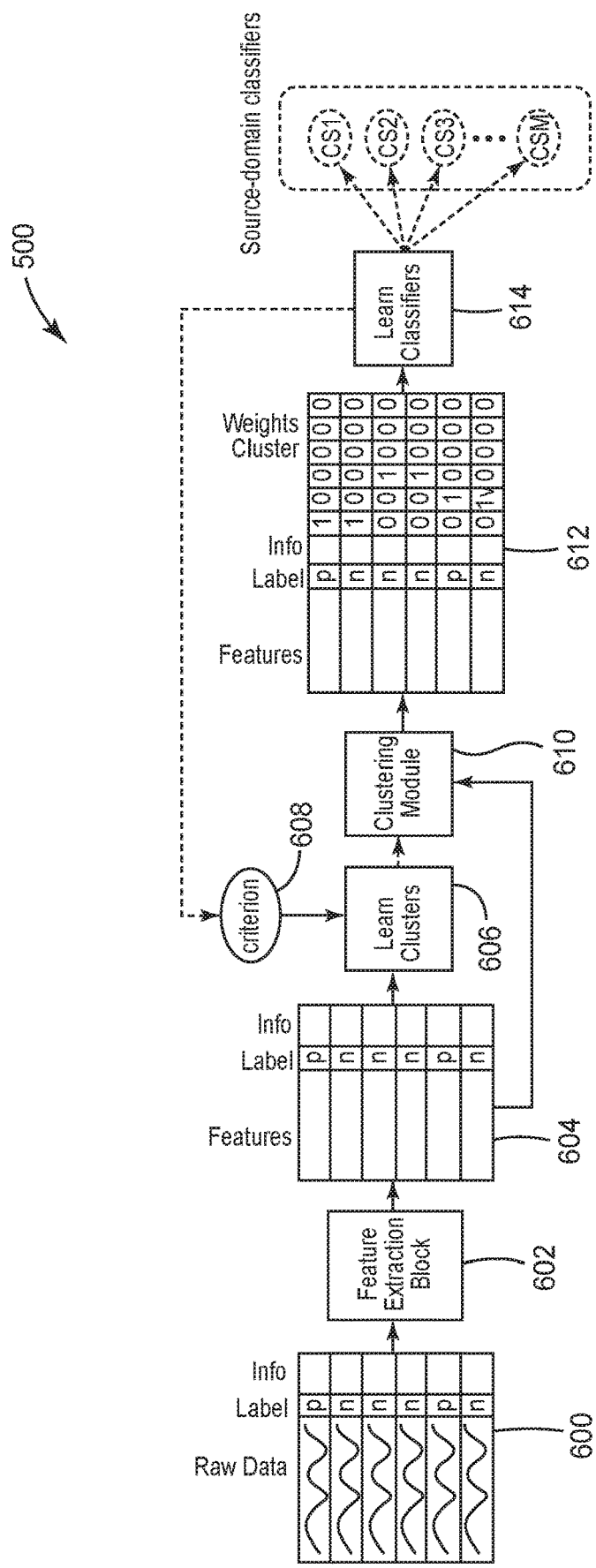
FIGS. 20A-20D further illustrate the technique shown in FIG. 19.

FIGS. 20A-20D further illustrate the technique shown in FIG. 19. In one example approach, source-domain training module 500 of FIG. 19 leverages historical data to make a prediction for new samples. One example is to use majority voting and take the average of predictions from classifiers previously trained on historical data. More advanced methods can be applied as well. One example is illustrated in FIG. 20A, where the first module is composed of several smaller blocks. The module takes labeled times-series samples from multiple source-domain users as its input and generates several classifiers (in the case of FIG. 20A, there are M ones). As in FIG. 20A, each times-series sample has three components: raw wave-form sequence, label (zero or one in the simple binary case), and the information about the user from whom the sample is taken. In the special case of the asthmatic user population, the user information may include the patient identification number or their asthma severity level.

In one example approach, data sequences representing samples 600 of time-series measurements first pass through the feature extraction block 602. This block only leverages the raw data component of each sample to create features 604. Therefore, even though, for instance, the user ID is available as part of the "info" component of samples, it will not be contributing to outcoming features of block 602. The number of features extracted by block 603 might be unlimited so that all the imaginable characteristics of waveforms are captured. However, in practice, the classification performance will be saturated after a limited number of features are included. Including more than that number of features will typically bring extra computational cost without providing further performance improvement.

Learn Cluster block 606 breaks the samples 600 into different clusters that are distinguished based on criterion block 608. The underlying assumption here is that the existing sample points are generated by a mixture of distributions. Therefore, before training any classifiers, it is important to cluster the samples and then train cluster-specific classifiers. As an example, the clustering criterion might be the user ID (given the assumption that all the samples from an individual user are generated from the same distribution, which might be distinct from other users' distributions). Other examples of clustering criterion might include asthma classification, location, gender, age, body-mass index, signal characteristics. Clustering module 610 is the outcome of block 606 and contains the clustering rules that are learned by the clustering module 610 (denoted by dashed lines).

In one example approach, module 500 applies clustering module block 610 to each data point to append a length-M vector of cluster weights to the data point. In one such example approach, the i-th weight element indicates how much that sample belongs to the i-th cluster. The clustering approach that is used in FIG. 20A might generate zero or one weights (called "hard clustering") or it may generate weights that are real-valued and lie between zero and one and add up to one (called "soft clustering").

Learn classifiers module 614 receives clustered feature data 612 and determines cluster-specific classifiers for data 612, which are denoted here by $CS\_1, CS\_2, \ldots, CS\_M$, where CS is used to denote classifiers that trained in the source domain and M denotes the number of such clusters. Note that the number of clusters M is a hyper-parameter that might be provided by the "criterion" block 608 at the clustering stage. The dashed lines here represent the "classification rules" that are learned by module 500.

Notice that the performance of the Learn Clusters block 606 shown in FIG. 20A has an impact on the performance of the following Learn Classifiers block 614. Therefore, where the training performance of the classification unit does not meet the acceptance criterion, it may be crucial to provide feedback to the clustering module 610 and improve the data clustering task. The arrow between learn classifiers 614 and criterion 608 in FIG. 20A represents the feedback. It may take several iterations for the two units until they reach near optimum clustering and classification rules that meet performance criterion.

Figure 20B:
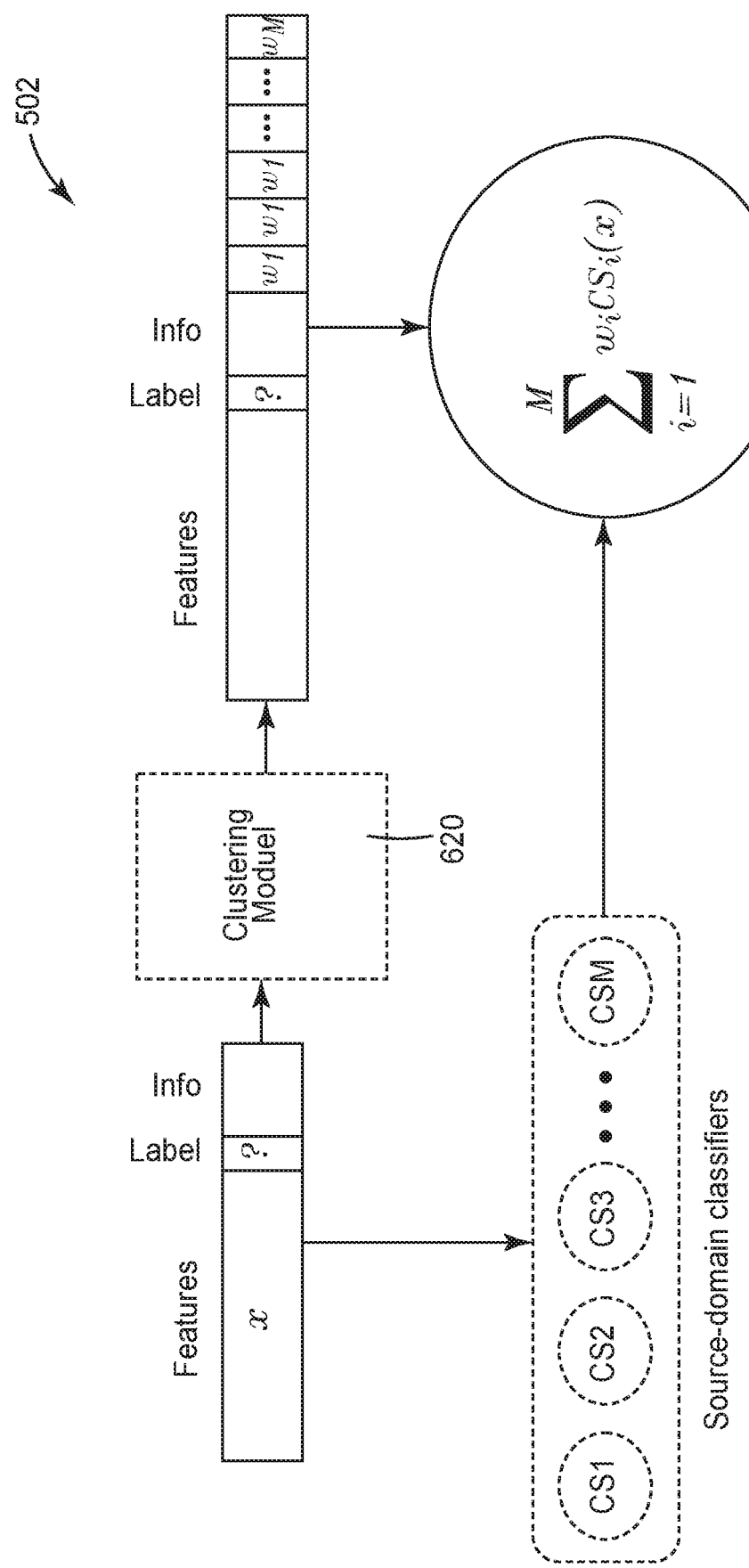

FIG. 20B illustrates one example approach for the source-domain prediction module of FIG. 19. In the example approach of FIG. 20B, classifiers trained by source-domain training module 500 are leveraged by source-domain prediction module 502 to predict the label of a new sample for which the correct label is unknown. As shown in FIG. 20B, the first block of this module (clustering module 620) is used to figure out the cluster that the sample belongs to. As explained in the previous section, the clustering weights, which are denoted by $w_1, w_2, \ldots, w_M$ in this figure, might be zero or one (in the case of hard clusters) or take any real values between zero and one (in the case of soft clusters). In either case, the weights must add up to one, i.e. $\Sigma_i w_i = 1$. Having obtained the cluster weights, the appended sample vector may be inputted to all the source-domain classifiers and its label will be predicted by them. Since, when it comes to prediction, each classifier $C_i$ can be viewed as a function that operates on sample feature vectors x, the predicted label by a classifier can be denoted as $C_i(x)$.

In some example approaches, the final prediction is a weighted average of all the M predictions from source-domain classifiers, where the weights come from clustering module. Therefore, $\hat{y}_i = \Sigma w_i C_i(x)$. The source-domain module is most accurate when the input sample belongs to the same distribution as the source-domain training data. When this assumption does not hold, the domain adaptation module (discussed next) may be leveraged to address the distributional difference between the source and target domains.

Figure 20C:
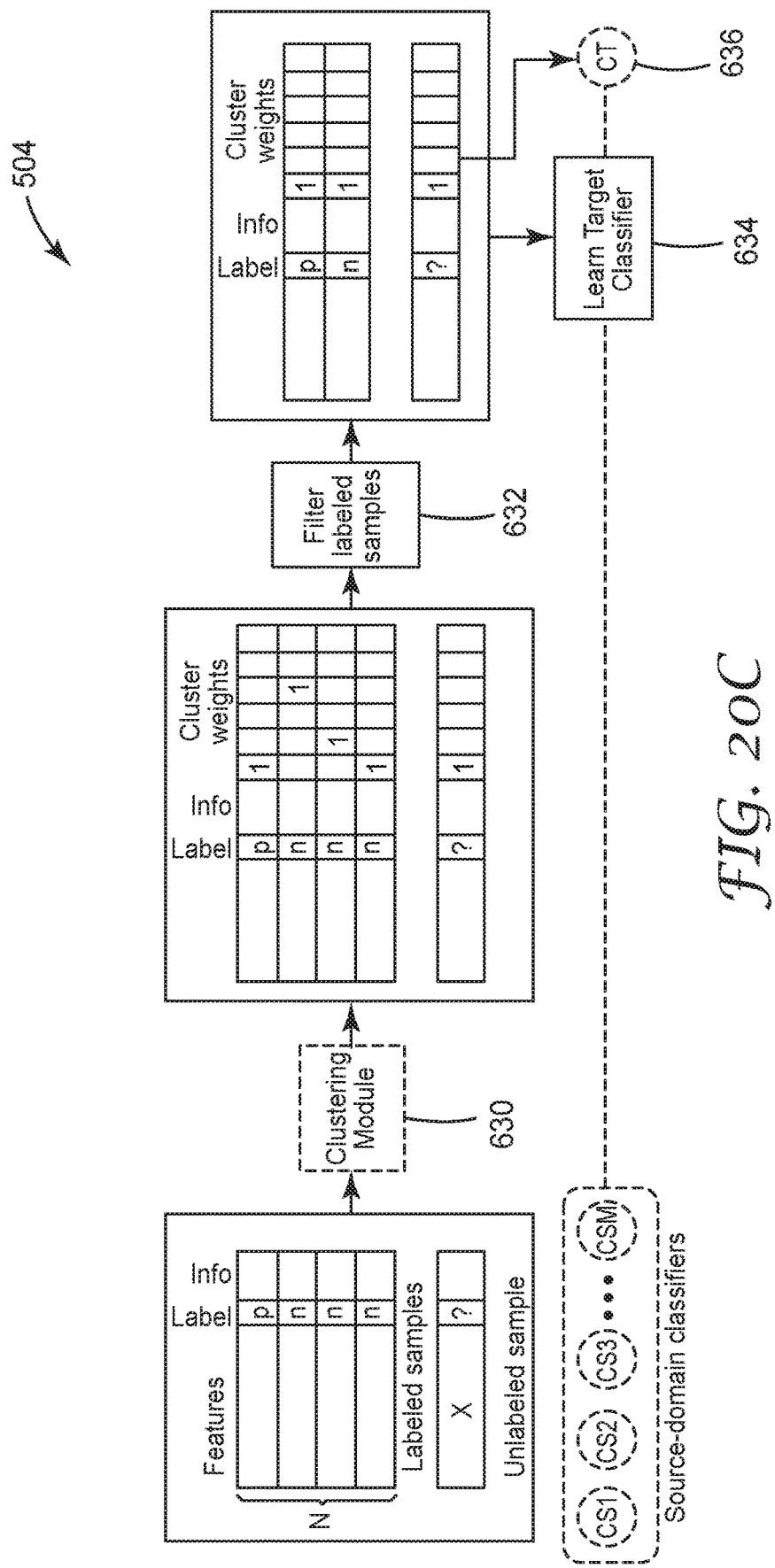

FIG. 20C illustrates one example approach for the domain adaptation module 504 of FIG. 19. In the example approach of FIG. 20C, module 504 leverages extra labeled data to create a classifier for classifier module 630. One may create a classifier from scratch using, for instance, the labeled data. The assumption is that a few labeled samples (N ones as in the FIG. 20C) as well as a single unlabeled sample are collected from the target-domain data distribution. The aim is to leverage the labeled samples to adjust the already-trained source-domain classifiers and obtain a new target-domain classifier, which is denoted by CT 636 in FIG. 20C. Like module 502, clustering block 630 is first used at 632 to filter out samples that do not belong to the same cluster as the unlabeled sample.

As mentioned earlier, after passing the data points through block 630, each sample is appended with a vector of length M that contains the clustering weights (here again we assume the weights are strictly equal to zero or one). Then, the Learn Target Classifier module 634 (described below) is leveraged to train the adapted classifier from the set of filtered target-domain samples. As the figure suggests, the learn target classifier block also takes the source-domain classifiers as its input and attempts to learn the adjusted classifier.

Figure 20D:
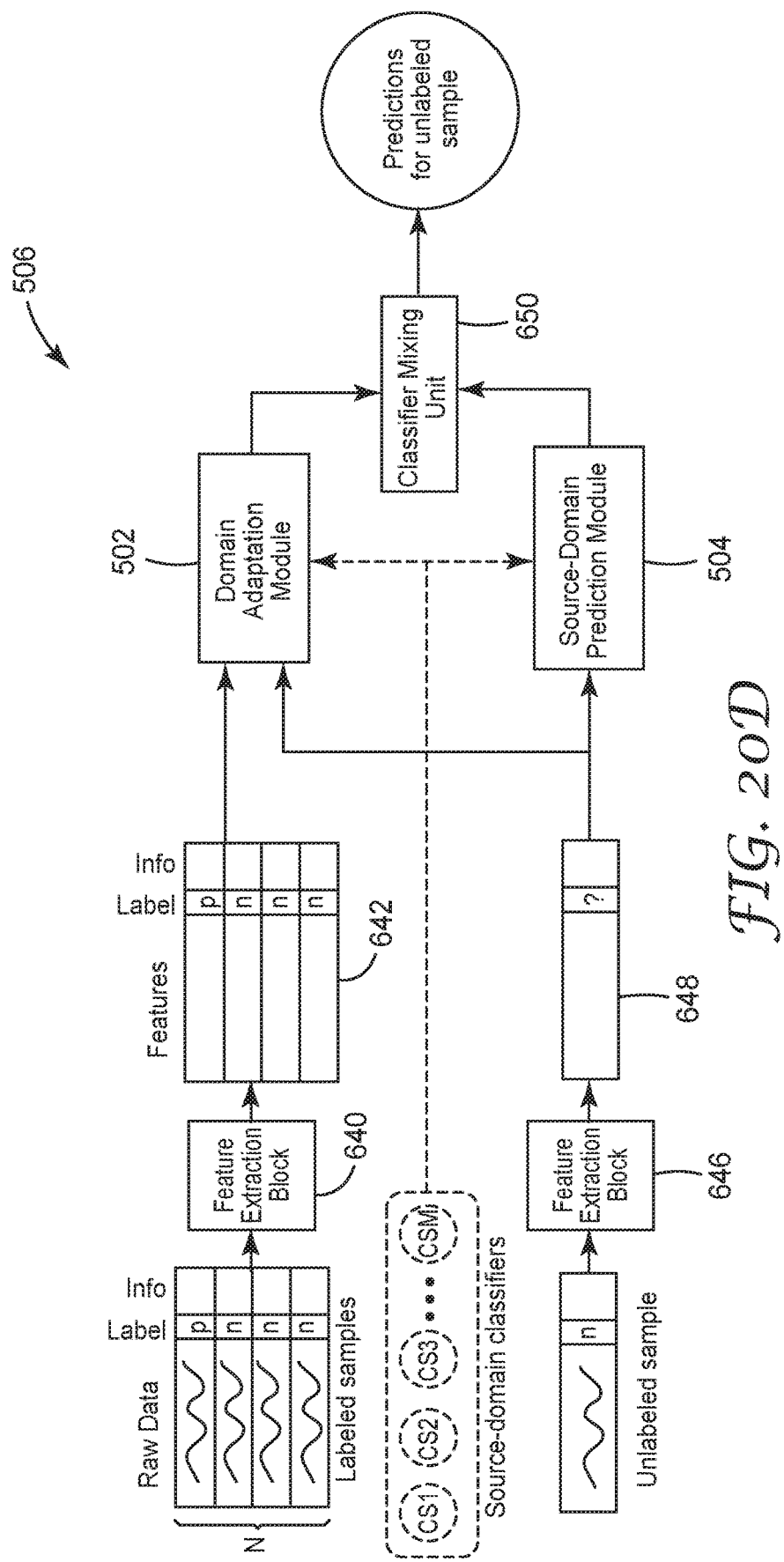

FIG. 20D illustrates one example approach for target-domain prediction module 506 in FIG. 19. In the example approach of FIG. 20D, the first step is to extract the features from raw times-series data via feature extraction block 646 and form feature vectors 648 for the collected target-domain samples. Then, depending on whether labeled samples are available (i.e. whether N>0 or not), two cases are possible. In the case where no labeled samples are available, user device 101 only uses the module 502 in FIG. 20B (i.e. the Source-Domain Prediction Module) to predict the labels for unlabeled samples. In this scenario, the prediction accuracy may be highly dependent on the similarity of the distribution of the target-domain samples with that of the source-domain samples that were leveraged when training the source-domain classifier.

In the case where N>0, features 642 and 648 are extracted from the target-domain data by feature extraction block 640 and 646, respectively. The feature data may go then through modules 502 and 504 and the predictions generated by the two modules may be aggregated by a classifier mixing unit 650. In one example approach, classifier mixing unit 650 simply averages the votes of the two modules 502 and 504. In another example approach, classifier mixing unit assigns different weights to the predictions of the modules 502 and 504 based on how reliable they are.

A technique for learning the target classifier will be discussed next. In one example approach, system 100 leverages a transfer learning technique. The leveraged transfer learning approach is a variant of the "TaskTrAdaboost" algorithm proposed by (Yao & Doretto, 2010). TaskTrAdaboost is based on an ensemble learning method that attempts to intelligently combine multiple classifiers from multiple source users to obtain a classifier for a new participant. Essentially, the new classifier may be a weighted average of the already-existing classifiers, where the value of (non-negative) weights is supposed to determine the amount of knowledge transfer from existing pool of users to the new one.

Like the TaskTrAdaboost method, the algorithm used to implement the learn target classifier 634 is a supervised ensemble method. Therefore, it requires a small set of labeled data collected from the device worn by the (new) target user. It deviates from TaskTrAdaboost in some ways that are described later in this section.

In one example approach, training module 392 requires as an input a set of source-domain classifiers that are already trained by the abundant data from (pre-existing) source users. The set of source classifiers will be denoted by $C=\{cs_1, cs_2, \ldots, cs_M\}$, where $cs_j$ is the jth source-domain classifier, as defined earlier.

Like Adaboost (Freund, Schapire, & Naoki, 1999), in one example approach, the algorithm initially assigns equal importance values to all the training data samples from the target user. Mathematically speaking, assume there are n training samples from the target user, each of which is characterized by the tuple $(x_i, y_i)$, for $1 \le i \le n$, where $x_i$ denotes the feature vector and $y_i$ represents the correct label of the sample. Then, the initial importance value for sample i is simply set to $$\beta_i = \frac{1}{n}.$$

Therefore, me summation or all importance values is equal to one, i.e.

$$\sum\nolimits_{i=1}^{n} \beta_i = 1.$$

In every iteration of the algorithm, all the source classifiers in C are applied to the labeled training data set of the target user and the weighted error of each classifier is computed by the following formula:

$$\epsilon_j = \sum\nolimits_{i=1}^{n} \beta_i \times 1[y_i \neq cs_j(x_i)],$$

where $1[\cdot]$ is equal to one if the operand is true and is zero otherwise. Then the classifier with the smallest value of error is chosen to go through the negative transfer test (which is one distinguishing factors from the TaskTrAdaboost algorithm).

In one example approach, the negative transfer test is as follows: if the weighted error value $\epsilon$ of the classifier c is smaller than a threshold $\gamma$ (by default set to $\gamma=0.5$), then (1) the classifier c is added to the initially-empty set S of final target classifiers, (2) the classifier c is removed from the initial pool of source classifiers C, and (3) a scaling factor $\alpha>0$ is computed for this classifier (to be discussed). Otherwise, the algorithm will be terminated due to negative transfer and the current set of final classifiers S, together with the corresponding scaling factors $\alpha$ will be returned. In case the set S is empty at this stage, it means that transfer learning does not work better than a random classifier for this user!

The weight of the classifier c is set to $$\alpha = \frac{1}{2} \log\left(\frac{1-\epsilon}{\epsilon}\right),$$

where $\epsilon$ is the error of the classifier computed in step c.

After each iteration, the importance values of the data points may be modified in the following way. For the sample i, the importance value will be set to $\beta_i = \beta_i \times \exp(-\alpha \cdot y_i \cdot \hat{y}_i)$, where $\hat{y}_i$ is the predicted label for this sample by the classifier c that has passed the negative transfer test for the current iteration. If the number of positive and negative samples in the training dataset is not nearly equal, we use a slightly different update mechanism. In this scenario, we update the importance values according to this formula $\beta_i = \theta_i \times \beta_i \times \exp(-\alpha \cdot y_i \cdot \hat{y}_i)$, where $\theta_i \in (0,1)$ is inversely proportional to the cardinality of the set of same-labeled samples in the training dataset. This approach for addressing the issue of imbalanced data is motivated by (Sun, Kamel, Wong, & Wang, 2007). The algorithm continues until the set C is empty or negative transfer happens. If $S=\{c_1, c_2, \ldots, c_T\}$ and $\{\alpha_1, \alpha_2, \ldots, \alpha_T\}$ denote the set of all selected classifiers and their corresponding scaling factors, with T denoting the total number of algorithm iterations, then the final target classifier is given by $$c^* = \sum\nolimits_{t=1}^{T} \alpha_t c_t.$$

Techniques for detecting events based on a combination of both value information and time information will be described next.

Figure 21:
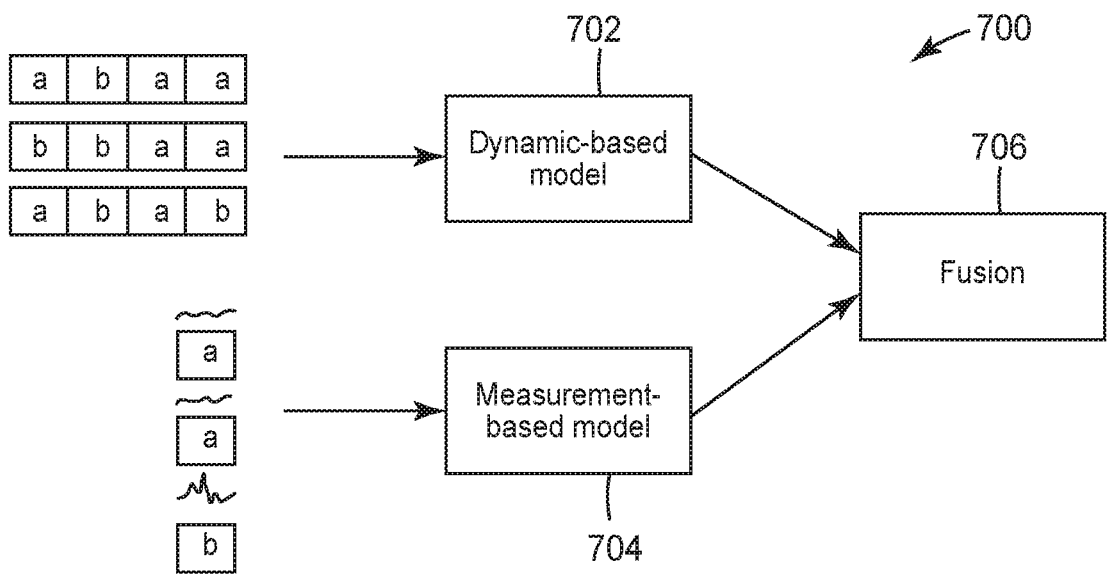
FIG. 21 is a block diagram illustrating a technique which leverages both the information residing in the current time data, such as the signal shape and features, and the information in the signal's dynamic and transitions between consecutive time intervals to yield more accurate algorithms for detection and prediction of the events.

The more system 100 extracts and leverages the information residing in the data received from sensor 104, the more accurate such algorithms become. FIG. 21 is a block diagram illustrating a technique which leverages both the information residing in the current time data, such as the signal shape and features, and the information in the signal's dynamic and transitions between consecutive time intervals to yield more accurate algorithms for detection and prediction of the events.

Time-series data is a special type of data which includes both value information and time information and applying mere machine learning methods such as classification might not result in acceptable results. Machine learning classifiers treat each time interval of data as an independent sample to extract the features and assign a label or class to it. So the dependency of the time intervals and the dynamic information residing in the data transitions are largely ignored in these methods.

A sensor system designed to monitor changes in the breathing patterns of individuals is an example of time-series data having both value information and time information. In the example of a power network, where the supplier wants to predict the future consumption of users, a dynamic model may leverage the patterns of consumption by users over a given number of days; the measurement model may leverage any kind of sensory data that is directly or indirectly related to power usage (for example, the current weather data or the number of people in the household could be used to develop the measurement-based model).

The approach shown in FIG. 21 uses dynamic-based algorithms to capture the dynamics of time series and to be used to improve the accuracy of measurement-based models such as classifiers. The approach shown in FIG. 21 leverages both the information residing in the current time data, such as the signal shape and features (measurement-based model), and the information in the signal history and transitions between consecutive time intervals (dynamic-based model). Then it fuses these two sources of information together intelligently to build more accurate algorithms for detection and prediction of events based on time-series measurement samples of one or more parameters associated with the biological function being monitored by a user device 101.

Dynamic-based models are used to capture the dynamics of time-series and to be more descriptive about the transition patterns of the data. Dynamic-based algorithms provide the ability to fuse information from a dynamic-based model with a measurement-based model to improve/filter the measurement-based results. In one example approach, the dynamic-based algorithm 700 shown in FIG. 21 is based on a dynamic-based model 702, a measurement-based model 704, and the fusion 706 of the two. The idea is to leverage both the information residing in the current time data, including the signal shape and features (measurement-based model) and the information in the signal dynamics and transitions between consecutive time intervals (dynamic-based model) to yield the best prediction. This framework may be used either for "detection" or "prediction" depending on what the input data and output data are.

Figure 22:
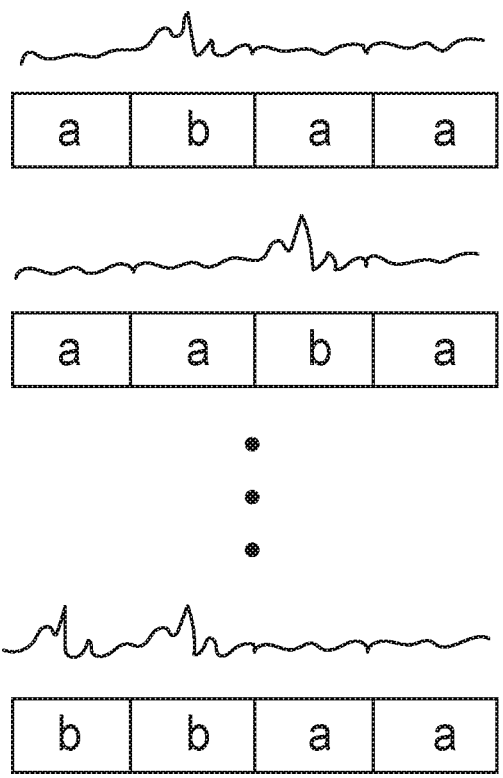
FIG. 22 illustrates time-series measurement samples received from a user device, in accordance with one aspect of the disclosure.

FIG. 22 illustrates time-series measurement samples received from a user device, in accordance with one aspect of the disclosure. As noted above and as shown in FIG. 22, the general format of sensor data in user device 101 is a collection of time series signals and the corresponding sequences of labels. In one example approach, dynamic-based model 702 receives the sequences of labels as the input which can also be considered as discrete-time and discrete-value time series. The measurement-based model 704 does not care about the order (transition) of the samples and so receives the samples as individual samples. Each sample is equal to a time interval of time series and a corresponding label.

As noted above, dynamic-based algorithms fuse information from dynamic-based models 702 and measurement-based models 704. Example dynamic-based algorithms include Markov models and hidden Markov model (HMM). In the Markov model, each state corresponds to an observable (physical) event. Such an approach may be too restrictive to be applicable to many problems of interest. HMM, however, extends the concept of Markov models to include the case where the observation is a probabilistic function of the state. HMM is a doubly embedded stochastic process with an underlying stochastic process that is not observable (it is hidden) but can only be observed through another set of stochastic processes that produce the sequence of observations.

In general, the data input to an HMM should be (a collection of) sequences; each sequence is a time series which is discrete in time. If the values (signal magnitude) are discrete and finite, they are called observation words. Each of the following examples deal with observation words.

In one example approach, the objective is to train a dynamic-based model 702 by using sequences of observations and then to use model 702 to predict the maximum likely observation for the next time interval when a sequence up to the current time interval is given. It some example approaches, only the data up to time t−1 is used for the training phase, leaving the data from time t and after unseen for the test phase. But note that for both training and test phases, the length of the sequences can be arbitrary (different t's) and the lengths are not necessarily all equal.

In one example approach, the objective in the test phase is to find the probability distribution over the observation words for time t+1, given the sequence of observations up to time t:

$$P(O_{t+1}|O_1, \ldots, O_t)$$

If an HMM is used as dynamic-based model 702, the objective in the test phase is formulated as follows:

$$P(O_{t+1}|O_1, O_t) = P(O_{t+1}|s_{t+1})P(s_{t+1}|O_1, \ldots, O_t) \quad (1)$$

$$= P[(O_{t+1})|s_{t+1})]P(s_{t+1}|s_t)P(s_t|O_1, \ldots, O_t)$$

$$= \text{emission probablity} \times \text{transition probability} \times$$
$$\text{likelihood from forward algorithm}$$

Figure 23:
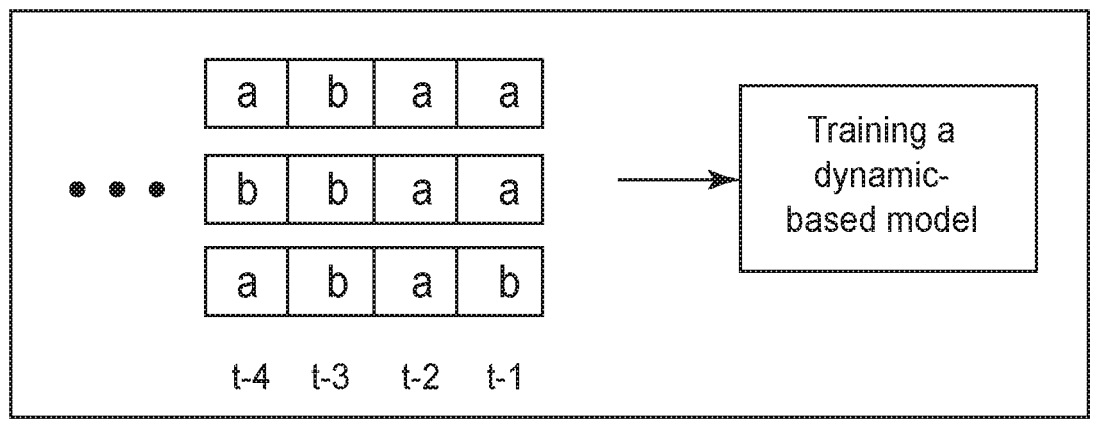
FIG. 23 illustrates a technique for training a dynamic-based model, in accordance with one aspect of the disclosure.
Figure 24:
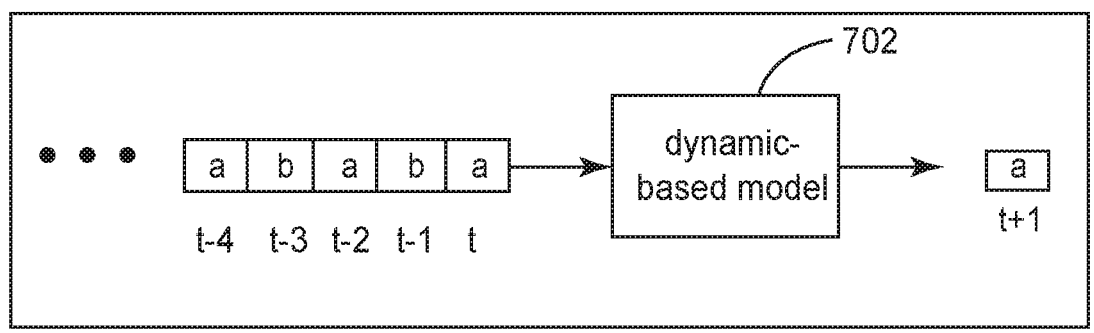
FIG. 24 illustrates applying the trained dynamic-based model 204 to sensor data received from sensor 104, in accordance with one aspect of the disclosure.

FIG. 23 illustrates a technique for training a dynamic-based model, in accordance with one aspect of the disclosure. FIG. 24 illustrates applying the trained dynamic-based model 702 to sensor data received from sensor 104, in accordance with one aspect of the disclosure. So the variations for the dynamic-based model are as follows: hidden Markov model (HMM), one model trained for all data, one model trained per cluster of data; higher-order Markov model, with a proper choice of order.

In the following example, system 100 trained an HMM model and used it to predict the Asthma Control Questionnaire (ACQ) score level and the reliever usage of the users each day.

Observations=(ACQ score per day, #Reliever usages per day)=(A,R)

Objective: Learn an HMM based on previous sequences of (A,R) for all users, and predict the next day (A,R) per user.

Quantize ACQ scores (A) and Reliever usages (R) per day into bins and build the following observation words:
Observation words={A0, A1, B0, B1, C0, C1, D0, D1}, where
A0: ACQ=[0,0.5) and no reliever usage
A1: ACQ=[0,0.5) and one or more reliever usage
B0: ACQ=[0.5,1.5) and no reliever usage
B1: ACQ=[0.5,1.5) and one or more reliever usage
C0: ACQ=[1.5,3) and no reliever usage
C1: ACQ=[1.5,3) and one or more reliever usage
D0: ACQ=[3,6] and no reliever usage
D1: ACQ=[3,6] and one or more reliever usage Build the training observation sequences out of the observation words and up to t−1. Train an HMM with 4 hidden states (representing the inner-body health status, but not necessarily interpretable) for all users (or per category of users).

The parameters required to train for this HMM=
4*4=16 transition probabilities
4*8=32 emission probabilities
4 priors (3 in fact, since they should add-up to 1)

In the test phase, a user's observation sequence up to t is given to the trained HMM to find the maximum likely observation word for t+1 using equation (1).

Figure 25:
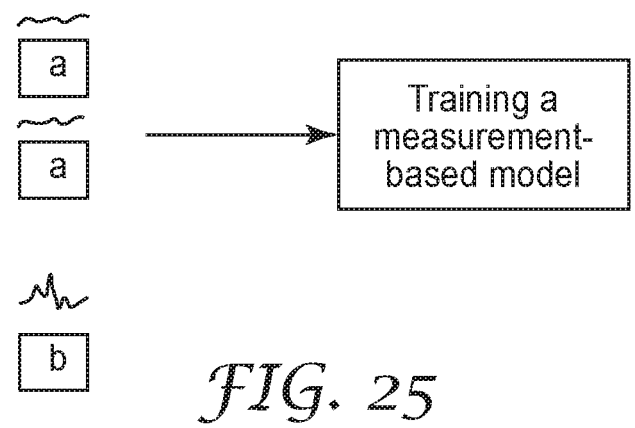
FIG. 25 illustrates a technique for training a measurement-based model, in accordance with one aspect of the disclosure.
Figure 26:
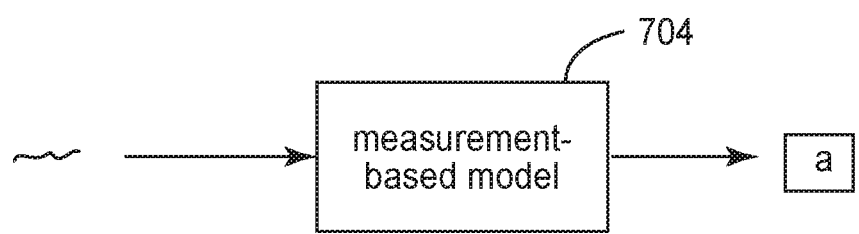
FIG. 26 illustrates applying a trained measurement-based model to sensor data received from a sensor, in accordance with one aspect of the disclosure.

FIG. 25 illustrates a technique for training a measurement-based model, in accordance with one aspect of the disclosure. FIG. 26 illustrates applying the trained measurement-based model 704 to sensor data received from sensor 104, in accordance with one aspect of the disclosure. The measurements-based models 704 work with the measurements/signals and labels/classes assigned to them to train a model. But in the test phase, no label exists for the signals and so the trained model 704 is used to assign labels to the signals. As an example of measurement-based models, machine learning classifiers can be used to classify the signals based on the features extracted from them and assign labels to them. If no label is available at all, the machine learning clustering methods would be used as the measurement-based model 704.

Fusion will be discussed next. In the example shown in FIG. 21, the outputs of dynamic-based model 702 and measurement-based model 704 are fused to improve and filter the results of each model individually. For the fusion, a linear combination of the results from dynamic-based and measurement-based models is used to determine a probability distribution that is weighted summed and for which the confidences (or training accuracies) are the weights:

$$k_1 P_1 + k_2 P_2$$

Note that this fusion model is not trained with data and is added to the framework after the training phase (for the test phase). Oher variations of fusion may use the same linear combination model but may, instead, be trained in the training phase in which the weights $k_1$ and $k_2$ are part of the hyper-parameters being trained using the data. Any non-linear combination of the probability distributions, e.g. $g(P_1, P_2)$, can be other variations considered for the fusion part.

Figure 27:
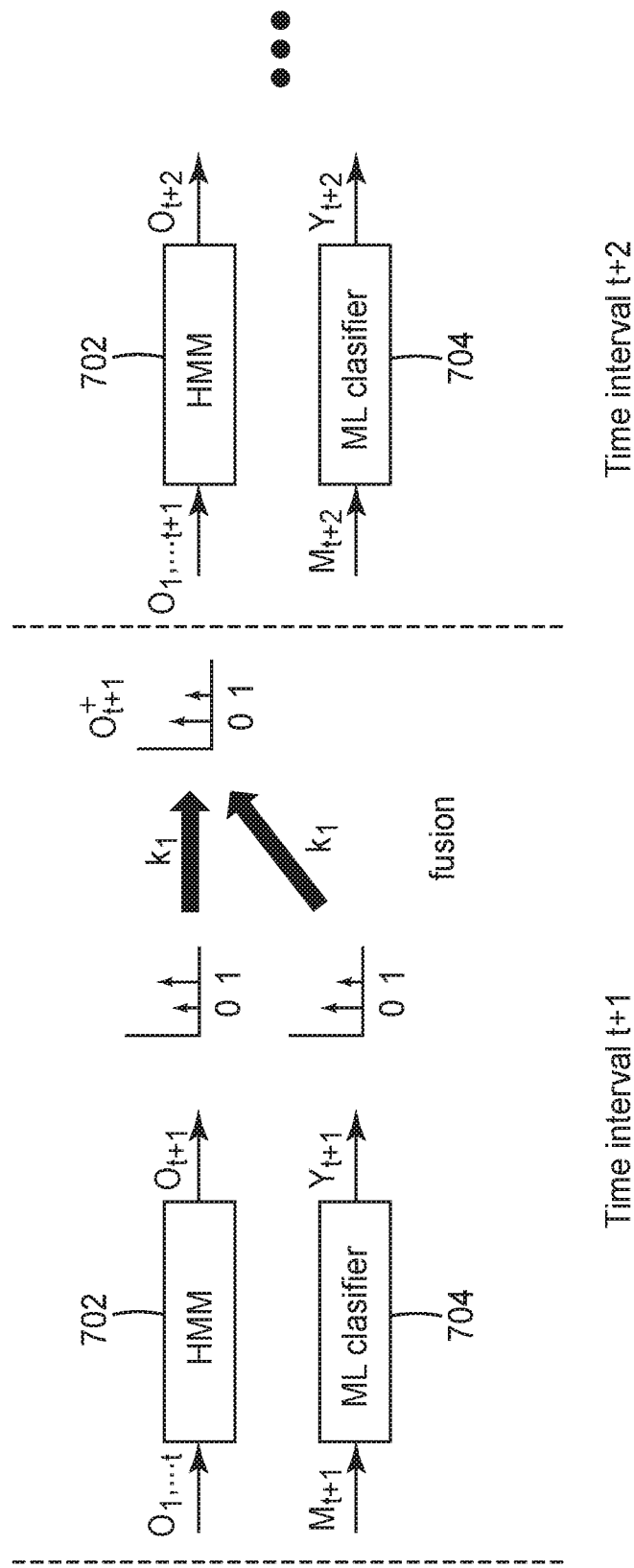
FIG. 27 illustrates a fusion example, in which the result of an HMM method as the dynamic-based model and the result of a machine learning classifier as the measurement-based model are fused together.

FIG. 27 illustrates a fusion example, in which the result of an HMM method as the dynamic-based model 702 and the result of a machine learning classifier as the measurement-based model 704 are fused together. M, Y, and O denote measurement signal, classifier result, and observation respectively. Note that the observations O's in the test phase can be partly from ground-truth labels and partly from fusion outputs, or may be all from the fusion output. If any historical ground-truth labels $O_{1,\ldots,t}$ are available for a test user, they are used to start the prediction from t+1, and the rest of $O_{t+1, \ldots}$ are built after fusion.

In the example of FIG. 27, the window size of fusion is 1, which can be advanced to higher orders in other variations. Moreover, if $M_t$ be the input instead of $M_{t+1}$, the exact same framework can be used for "prediction" instead of "detection".

A framework for detecting and predicting respiratory events such as an asthma attack and other kinds of respiratory events which compromise the breathing patterns of a human will be described next. For the purposes of clarity the "asthma attack" is simply a concrete example of detection; the framework may be applied to other physiological signals.

In an asthma attack, it can be difficult for air to move out of the lungs, causing symptoms such as coughing, wheezing, chest tightness, shortness of breath etc. Duration and symptoms of an asthma attack are very different across patients. While asthma patients are largely categorized as mild, moderate and severe, there is no definite pattern to describe triggers and symptoms across different patients, making it a very hard pattern recognition problem. Simultaneously, varying durations of the asthma attack event introduce added difficulty as it is hard to pin-point the exact time of the event. Variations largely depend on what caused the attack and how long the airways have been inflamed. Episodes may last only a few minutes to hours.

A key to helping asthma patients is to enable them with technology that can recognize an asthma flare up early enough for them to intervene, such as by using a rescue inhaler. Furthermore, an accurate tracking framework opens the door for trigger analysis using advance data analytics tools to deploy prevention strategies.

Figure 28:
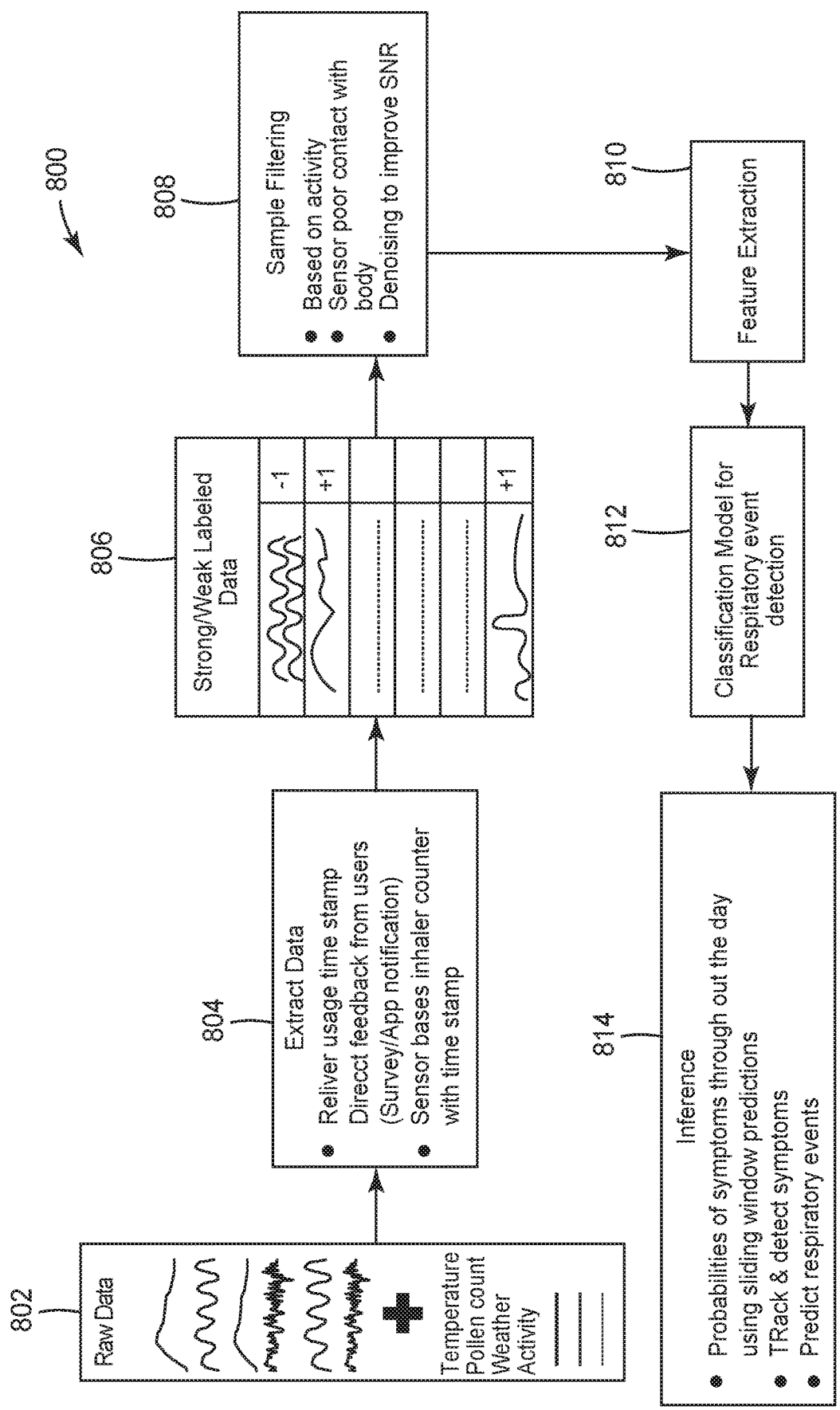
FIG. 28 illustrates a framework in which a monitoring system receives raw data from a sensor, in accordance with one aspect of the disclosure.

FIG. 28 illustrates a framework 800 in which system 100 receives raw data 802, in accordance with one aspect of the disclosure. In the example shown in FIG. 28, raw data 802 includes sensor data captured by sensor 104, weak labels associated with the event, and side information such as environmental information and demographic information. In the example approach of FIG. 28, feature extraction 804 extracts measurement samples from raw data 802, delivering signal features based on the sensor data as well as feedback from users 102, time stamps and inhaler use information. In the example approach of FIG. 28, one or more algorithms are applied at 806 to detect strong and weak labeled data (such as discussed in the discussion of FIGS. 3-13 above). Usable signals are filtered at 808 and features are extracted from the usable samples at 810. A check is performed at 812 to determine is a respiratory event occurred and inferences are made at 814 on the likelihood of symptoms throughout the day and the possibility of respiratory events.

In one example approach, users 102 are asked to wear a sensor 104 such that a proxy physiological signal can be measured including but not limited to pressure as the person's breath, accelerometer capturing activity, and body temperature. Notionally, one sample in raw data could mean one type of signal. Or the raw data 802 may include multiple signals stacked together such as pressure data stacked with accelerometer (x, y, and z axes) data. The raw data can also include side information such as environment temperature and pressures, various allergens counts in the atmosphere etc.

Figure 29:
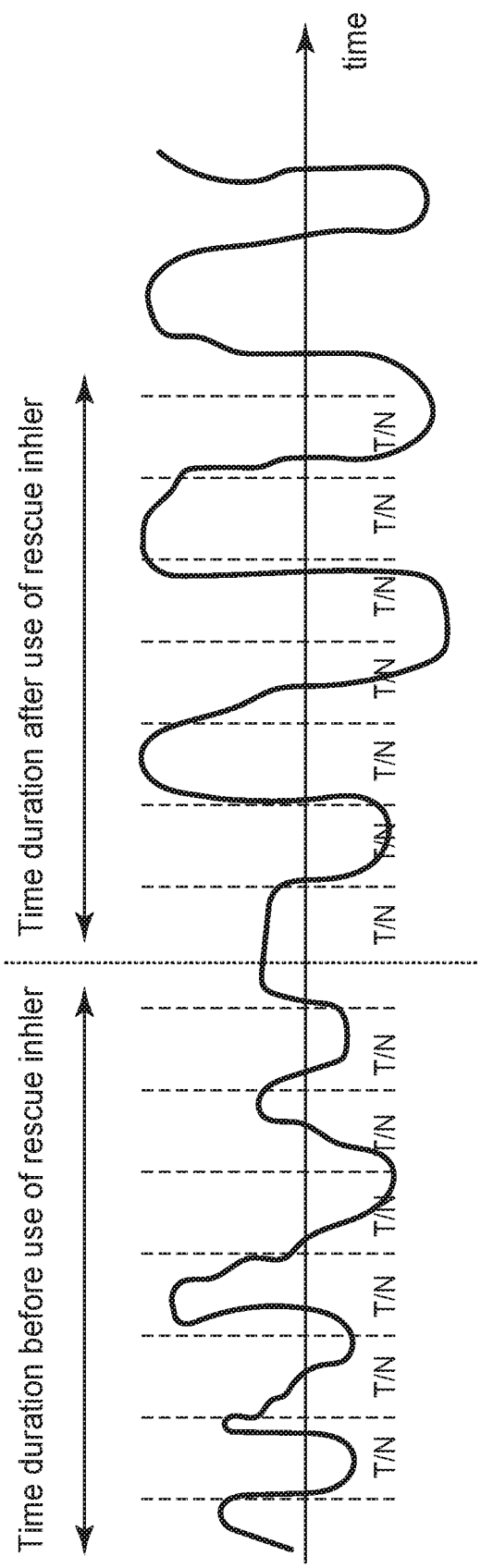
FIG. 29 illustrates occurrence of an intervention in a stream of time-series measurement samples, in accordance with one aspect of the disclosure.

Asthma events vary in duration, episodes may last only a few minutes to hours. In one example approach, the example approach of FIG. 28 leverages medical intervention to establish the notion of peak of an ongoing event. For instance, in the example of FIG. 28, computing device 106 uses the time stamp to indicate when the subject used his/her rescue inhaler to treat the ongoing attack. FIG. 29 illustrates occurrence of an intervention in a stream of time-series measurement samples, in accordance with one aspect of the disclosure. The underlying assumption is that the patient will use the rescue inhaler when they realized that the symptoms were getting worse and that they needed immediate. Rescue inhalers instantly alleviate the asthma symptoms. The notification (time stamp) of rescue inhaler use can, in some example approaches, be provided by the patient as direct feedback in writing, digitally through a survey application, or a sensor deployed in the inhaler itself which can transfer the usage data through the cloud.

There may be uncertainty around the starting point of the asthma event and when it was completely over. In the example approach of FIG. 28, system 100 deals with this uncertainty by analyzing samples from the raw data around the rescue inhaler time stamp shown in FIG. 29. In one such approach, the sample duration "T" before and after rescue inhaler is a parameter in the proposed framework which can be optimized through experiments across various subjects. The data from before the rescue inhaler time period is assigned a label of −1, while +1 labels are assigned to the sample from after rescue inhaler usage. There are various ways one can create a labeled data matrix where the last column corresponds to the label of the sample:

1. Use before and after sample of length T each as one example of each label
2. Create multiple samples of length T/N from before rescue inhaler use raw data all labeled as −1, and another set of T/N samples from after rescue data all labeled as +1, where N is used to further divide the sample of length T into smaller repeating units (e.g. cycles) for analysis (see FIG. 3). N can also be treated as a parameter to be determined by the experiments
3. Detect individual breaths in raw data and label them according to occurrence before and after the use of rescue inhaler Before training the model for event detection, system 100 filters the data based on its quality. This may be critical to guarantee the accuracy and robustness of the trained model. Bad quality data may impact performance of machine learning algorithms and such results can become less reliable. Some of the reasons that can result in degraded data for a wearable sensor are when the sensor 104 is not worn, sensor 104 not worn properly and has poor contact with the body, sensor 104 is worn but the subject is performing a physical activity which can affect the sensor measurements. or breathing data may have been modulated with low frequency activity.

As noted above, various features can be extracted from the samples in the labeled data matrix to be used in the downstream pipeline. These features may include simple features such as number of peaks, value of the peaks, inhalation time, and exhalation time as well as complex signal processing features including but not limited to autocorrelation values at different lags, and Fourier coefficients. Features can be extracted from individual sensors such as pressure, accelerometer (x, y, z) or from a combination of signals by applying other methods such as Cross Spectral Density. These signal-based features may also be appended using side information such as environment temperature and pressures, and various allergen counts in the atmosphere etc.

After sample filtration and feature extraction, system 100 moves to a supervised classification problem with positive (before inhaler use) and negative (after inhaler use) labeled data. If the prediction models are intended to be generalizable (similar models used across subjects), features from multiple sensors (subjects) may be stacked for creating the model.

There are various machine learning methods such as random forest, logistic regression, support vector machines, recurrent neural networks, that can be leveraged to train a model to detect if a sample corresponds to before/after usage class. One may also use different weighting for the samples. In one example approach, for example, system 100 assigning lower weights to samples that are further away from the rescue inhaler time stamp to reduce their impact on the detection of the event.

Inference block 814 is the final block of the proposed framework shown in FIG. 28. The trained model may be used for various inference tasks. For example—severity of the asthma symptom can be inferred through the confidence of the model prediction. The analysis can involve a sliding window prediction over long periods of time.

Trained models may also be used to detect asthma events in real time. This approach allows users to track their overall health without manual logging of their symptoms. Finally, accurate detection models along with dynamic models can be leveraged to predict the future asthma attacks. Also note that the training phase can repeat as much as desired. In one example approach, every time a new sample is captured, the sample is processed in a "batch processing" mode where all the samples are re-processed or in a "update" mode where the model is updated with the new sample obtained.

The example approach shown in FIGS. 28 and 29 provides a simple mechanism for labeling samples as a function of an outside activity. Such an approach can be used as well for other indicia susceptible for labelling data.

An example system for respiratory monitoring may include a sensor, where the sensor monitors at least one respiratory related parameter; a computing device connected to the sensor, where the computing device includes a processor, where the processer detects a first breathing state based on the at least one respiratory related parameter received from the sensor; a user interface, where the user interface receives user input related to the first breathing state, and where the processor modifies the detection of one or more breathing states based on the user input.

An example non-transitory computer-readable storage medium that stores computer system executable instructions that, when executed, may configure a processor to: detect a first breathing state based on at least one respiratory related parameter received from a sensor, where the sensor monitors the at least one respiratory related parameter; and modify the detection of one or more breathing states based on user input related to the first breathing event, where a user interface receives the user input.

An example method includes receiving historical sensor data associated with a sensor device that monitors a biological function, the historical sensor data representing historical time-series measurement samples of one or more parameters associated with the biological function being monitored by the sensor device; extracting feature data from the historical sensor data, the feature data representing two or more features of the historical time-series measurement samples; assigning the historical time-series measurement samples to clusters; generating cluster-specific source-domain classifiers for each cluster based on the extracted feature data; receiving, as target-domain samples, unlabeled samples of target user sensor data, the target user sensor data representing time-series measurement samples of the one or more parameters associated with the biological function of a target user being monitored by the sensor device; assigning a cluster-identifier to each unlabeled target-domain sample, the cluster-identifier including information identifying a cluster-specific source-domain classifier associated with the sample to be labeled; receiving labeled samples of target user sensor data, the labeled samples representing time-series measurement samples of the one or more parameters associated with the biological function of the target user being monitored by the sensor device; extracting feature data from the labeled samples associated with the target user, the feature data representing two or more features of the labeled samples; and generating cluster-specific target-domain classifiers for each cluster based on the source-domain classifiers and the extracted feature data associated with the labeled samples. In one example approach, the method further includes training a machine learning algorithm to label unlabeled samples of the target user sensor data based on the source-domain and the target-domain classifiers.

An example method of labeling sensor data includes receiving sensor data associated with a sensor device that monitors a biological function, the sensor data representing time-series measurement samples of one or more parameters associated with the biological function being monitored by the sensor device; receiving sensor data representing an intervention known to cause a change in the time-series measurement samples; determining time-series measurement samples that fall before the intervention and time-series measurement samples that fall after the intervention; labeling the time series measurement samples that fall before the inhaler use as pre-intervention samples; labeling the time-series measurement samples that fall after the intervention as post intervention samples; and training a detection algorithm based on the labeled samples.

In one example approach, the time-series measurement samples are breathing measurement samples and wherein the intervention is inhaler use. In one example approach, training the detection algorithm includes reducing the contribution of the labeled data as a function of a time measured from the intervention. In one example approach, training the detection algorithm includes modifying the detection algorithm to reflect environmental information received with the sensor data. In one example approach, training the detection algorithm includes modifying the detection algorithm to reflect demographic information received with the sensor data. In one example approach, training the detection algorithm includes analyzing measurement samples captured at approximate the same time as the intervention and modifying an intervention time stamp based on the analysis.

In one example approach, training the detection algorithm includes creating a labeled data matrix. In one such example approach, the labeled data matrix includes two or more measurement samples from before the intervention. In another such example approach, the labeled data matrix includes two or more measurement samples from after the intervention.

An example method includes receiving sensor data associated with a sensor device that monitors a biological function, the sensor data representing time-series measurement samples of one or more parameters associated with the biological function being monitored by the sensor device, wherein the sensor data includes usable and unusable samples of the time-series measurements; extracting data representing two or more features of samples of the time-series measurements; filtering the extracted data, wherein filtering includes eliminating outliers in the extracted data based on an expected outlier ratio; and training a machine learning algorithm to identify events based on the filtered extracted data. In one such example approach, eliminating outliers in the extracted feature data includes applying an isolation forest technique to the extracted feature data. In one such example approach, training the machine learning algorithm includes applying a one-class support vector machine (SVM) technique to the filtered extracted feature data. In one such example approach, training the machine learning algorithm includes determining clusters of users and applying a one-class support vector machine (SVM) technique to the filtered extracted feature data to determine a machine learning algorithm for each cluster. In one such example approach, the time-series measurement samples include measurement samples associated with breathing, wherein the measurement samples associated with breathing include measurements of abdominal movement and of acceleration. In one such example approach, the time-series measurement samples include measurement samples associated with breathing and wherein the features are selected from one or more parameters of the received sensor data, the parameters including relative amplitude, duration, volume of breath, slope, shape, inhalation time, exhalation time, inhalation to exhalation ratio, sample consistency and sample reconstruction error.

In one such example approach, training the machine learning algorithm includes receiving labeled sensor data, the labeled sensor data including first labels identifying usable and unusable samples in the labeled sensor data; assigning second labels to samples in the labeled sensor data, wherein assigning second labels includes applying the machine learning algorithm to the labeled sensor data to detect usable and unusable samples in the labeled sensor data; and modifying the expected outlier ratio as a function of discrepancies between the first and second labels.

In one example approach, the labeled sensor data includes data labeled as a function of a concurrent alternate measurement of the biological parameters. In one example approach, the time-series measurement samples include measurement samples associated with breathing and receiving labeled sensor data includes concurrently capturing measurement samples associated with breathing via the sensor device and via a breath measurement apparatus and labelling the breath measurements captured by the sensor device based on the measurement samples associated with breathing captured by the breath measurement apparatus. In one such example approach, the breath measurement device is a respirator.

In one example approach, a method includes receiving sensor data associated with a sensor device that monitors a biological function, the sensor data representing time-series measurement samples of one or more parameters associated with the biological function being monitored by the sensor device, applying a dynamic-based model to the sensor data; applying a measurement-based model to the sensor data; and fusing the dynamic-based model and the measurement-based model.

In one such example approach, fusing includes assigning weights to the two models and determining a fusion model based on a weighted sum of the elements of the dynamic-based model and the measurement-based model. In another such example approach, fusing is a function of observations and ground-truth labels. In another such example approach, the time-series measurements include breath measurements, wherein the breath measurements include measurements of pressure and of acceleration.

In another such example approach, the time-series measurements include breath measurements and wherein features are selected from one or more parameters of the received sensor data including relative amplitude, duration, volume of breath, slope, shape, inhalation time, exhalation time, inhalation to exhalation ratio, sample consistency and sample reconstruction error.

In another such example approach, training the machine learning algorithm includes receiving labeled sensor data, the labeled sensor data including first labels identifying usable and unusable samples in the labeled sensor data; assigning second labels to samples in the labeled sensor data, wherein assigning second labels includes applying the machine learning algorithm to the labeled sensor data to detect usable and unusable samples in the labeled sensor data; and modifying the expected outlier ratio as a function of discrepancies between the first and second labels.

In one such example approach, the labeled sensor data includes data labeled as a function of an alternate measurement of the biological parameters.

In one such example approach, the time-series measurements include breath measurements, and receiving labeled sensor data includes capturing breath measurements concurrently via the sensor and via a respirator and labelling the breath measurements captured by the sensor based on the breath measurements captured by the respirator.

Exemplary Embodiments

In exemplary embodiment A1, a method includes receiving sensor data associated with a sensor device that monitors a biological function, the sensor data representing time-series measurement samples of one or more parameters associated with the biological function being monitored by the sensor device, wherein the sensor data includes usable and unusable samples of the time-series measurements; extracting data representing two or more features of samples of the time-series measurements; filtering the extracted data, wherein filtering includes eliminating outliers in the extracted data based on an expected outlier ratio; and training a machine learning algorithm to identify events based on the filtered extracted data.

In exemplary embodiment A2, the method of exemplary embodiment A1, wherein eliminating outliers in the extracted feature data includes applying an isolation forest technique to the extracted feature data.

In exemplary embodiment A3, the method of any of exemplary embodiments A1 or A2, wherein training the machine learning algorithm includes applying a one-class support vector machine (SVM) technique to the filtered extracted feature data.

In exemplary embodiment A4, the method of any of exemplary embodiments A1, A2 or A3, wherein training the machine learning algorithm includes determining clusters of users and applying a one-class support vector machine (SVM) technique to the filtered extracted feature data to determine a machine learning algorithm for each cluster.

In exemplary embodiment A5, the method of any of exemplary embodiments A1-A4, wherein the time-series measurement samples include measurement samples associated with breathing, wherein the measurement samples associated with breathing include measurements of abdominal movement and of acceleration.

In exemplary embodiment A6, the method of any of exemplary embodiments A1-A5, wherein the time-series measurement samples include measurement samples associated with breathing and wherein the features are selected from one or more parameters of the received sensor data, the parameters including relative amplitude, duration, volume of breath, slope, shape, inhalation time, exhalation time, inhalation to exhalation ratio, sample consistency and sample reconstruction error.

In exemplary embodiment A7, the method of any of exemplary embodiments A1-A6, wherein training the machine learning algorithm includes receiving labeled sensor data, the labeled sensor data including first labels identifying usable and unusable samples in the labeled sensor data; assigning second labels to samples in the labeled sensor data, wherein assigning second labels includes applying the machine learning algorithm to the labeled sensor data to detect usable and unusable samples in the labeled sensor data; and modifying the expected outlier ratio as a function of discrepancies between the first and second labels.

In exemplary embodiment A8, the method of any of exemplary embodiments A1-A7, wherein eliminating outliers in the extracted feature data includes applying an isolation forest technique to the extracted feature data.

In exemplary embodiment A9, the method of any of exemplary embodiments A1-A8, wherein the labeled sensor data includes data labeled as a function of a concurrent alternate measurement of the biological parameters.

In exemplary embodiment A10, the method of any of exemplary embodiments A1-A9, wherein the time-series measurement samples include measurement samples associated with breathing and wherein receiving labeled sensor data includes concurrently capturing measurement samples associated with breathing via the sensor device and via a breath measurement apparatus and labelling the breath measurements captured by the sensor device based on the measurement samples associated with breathing captured by the breath measurement apparatus.

In exemplary embodiment A11, a system comprises a sensor device, wherein the sensor device monitors at least one biological function; one or more processors connected to the sensor device; and memory connected to the one or more processors, wherein the memory includes instructions that, when executed by one or more of the processors, cause the processors to receive sensor data from the sensor device, the sensor data representing time-series measurement samples of one or more parameters associated with the biological functions being monitored by the sensor device, wherein the sensor data includes usable and unusable samples of the time-series measurements; extract data representing two or more features of samples of the time-series measurements; filter the extracted data, wherein filtering includes eliminating outliers in the extracted data based on an expected outlier ratio; and train a machine learning algorithm to identify events based on the filtered extracted data.

In exemplary embodiment A12, a system comprises the system of exemplary embodiment A11, wherein the sensor device includes a respirator.

In exemplary embodiment A13, a system comprises the system of any of exemplary embodiments A11 or A12, wherein training the machine learning algorithm includes receiving labeled sensor data, the labeled sensor data including first labels identifying usable and unusable samples in the labeled sensor data; assigning second labels to samples in the labeled sensor data, wherein assigning second labels includes applying the machine learning algorithm to the labeled sensor data to detect usable and unusable samples in the labeled sensor data; and modifying the expected outlier ratio as a function of discrepancies between the first and second labels.

In exemplary embodiment A14, a system comprises the system of any of exemplary embodiments A11, A12 or A13, wherein the time-series measurement samples include measurement samples associated with breathing, and wherein training the machine learning algorithm includes receiving labeled sensor data includes concurrently capturing measurement samples associated with breathing via the sensor device and via a breath measurement apparatus; and labelling the breath measurements captured by the sensor device based on the measurement samples associated with breathing captured by the breath measurement apparatus.

In exemplary embodiment A15, a system comprises the system of any of exemplary embodiments A11-A14, wherein the sensor device includes sensors for taking time-series measurements of abdominal movement and of acceleration.

In exemplary embodiment A16, a non-transitory computer-readable storage medium stores instructions that, when executed, cause a processor to receive sensor data from the sensor device, the sensor data representing time-series measurement samples of one or more parameters associated with the biological functions being monitored by the sensor device, wherein the sensor data includes usable and unusable samples of the time-series measurements; extract data representing two or more features of samples of the time-series measurements; filter the extracted data, wherein filtering includes eliminating outliers in the extracted data based on an expected outlier ratio; and train a machine learning algorithm to identify events based on the filtered extracted data.

In exemplary embodiment A17, a non-transitory computer-readable storage medium includes the instructions of exemplary embodiment A16, wherein the instructions that, when executed, cause a processor to train the machine learning algorithm include instructions that, when executed, cause a processor to receive labeled sensor data, the labeled sensor data including first labels identifying usable and unusable samples in the labeled sensor data; assign second labels to samples in the labeled sensor data, wherein assigning second labels includes applying the machine learning algorithm to the labeled sensor data to detect usable and unusable samples in the labeled sensor data; and modify the expected outlier ratio as a function of discrepancies between the first and second labels.

In exemplary embodiment A18, a computing device is configured to perform the methods of any of exemplary embodiments A1-A10.

In exemplary embodiment A19, a system is configured to perform the methods of any of exemplary embodiments A1-A10.

In exemplary embodiment A20, a non-transitory computer readable medium, computing system, or apparatus is configured to perform any of the methods of any of exemplary embodiments A1-A10.

In exemplary embodiment B1, a method includes receiving sensor data associated with a sensor device that monitors a biological function, the sensor data representing time-series measurement samples of one or more parameters associated with the biological function being monitored by the sensor device; applying a dynamic-based model to the sensor data; applying a measurement-based model to the sensor data; and fusing the dynamic-based model and the measurement-based model.

In exemplary embodiment B2, the method of exemplary embodiment B1, wherein fusing includes assigning weights to the two models and determining a fusion model based on a weighted sum of the elements of the dynamic-based model and the measurement-based model.

In exemplary embodiment B3, the method of any of exemplary embodiments B1 or B2, wherein fusing is based on one or more of observation labels and ground-truth labels.

In exemplary embodiment B4, the method of any of exemplary embodiments B1, B2 or B3, wherein the time-series measurements include breath measurements, wherein the breath measurements include measurements of pressure and of acceleration.

In exemplary embodiment B5, the method of any of exemplary embodiments B1-B4, wherein the time-series measurements include breath measurements and wherein features are selected from one or more parameters of the received sensor data including relative amplitude, duration, volume of breath, slope, shape, inhalation time, exhalation time, inhalation to exhalation ratio, sample consistency and sample reconstruction error.

In exemplary embodiment B6, the method of any of exemplary embodiments B1-B5, wherein training the machine learning algorithm includes receiving labeled sensor data, the labeled sensor data including first labels identifying usable and unusable samples in the labeled sensor data; assigning second labels to samples in the labeled sensor data, wherein assigning second labels includes applying the machine learning algorithm to the labeled sensor data to detect usable and unusable samples in the labeled sensor data; and modifying the expected outlier ratio as a function of discrepancies between the first and second labels.

In exemplary embodiment B7, the method of any of exemplary embodiments B1-B6, wherein the labeled sensor data includes data labeled as a function of an alternate measurement of the biological parameters.

In exemplary embodiment B8, the method of any of exemplary embodiments B1-B7, wherein the time-series measurements include breath measurements, and wherein receiving labeled sensor data includes capturing breath measurements concurrently via the sensor and via a respirator and labelling the breath measurements captured by the sensor based on the breath measurements captured by the respirator.

In exemplary embodiment B9, a system includes a sensor device, wherein the sensor device monitors at least one biological function; one or more processors connected to the sensor device; and memory connected to the one or more processors, wherein the memory includes instructions that, when executed by one or more of the processors, cause the processors to receive sensor data associated with a sensor device that monitors a biological function, the sensor data representing time-series measurement samples of one or more parameters associated with the biological function being monitored by the sensor device; apply a dynamic-based model to the sensor data; apply a measurement-based model to the sensor data; and fuse the dynamic-based model and the measurement-based model.

In exemplary embodiment B10, the system of exemplary embodiment B9, wherein the time-series measurements include breath measurements, and wherein receiving labeled sensor data includes capturing breath measurements concurrently via the sensor and via a respirator and labelling the breath measurements captured by the sensor based on the breath measurements captured by the respirator.

In exemplary embodiment B11, the system of any of exemplary embodiments B9 or B10, wherein the instructions that, when executed by one or more of the processors, cause the processors to fuse the dynamic-based model and the measurement-based model include instructions that, when executed by one or more of the processors, cause the processors to assign weights to the two models and to determine a fusion model based on a weighted sum of the elements of the dynamic-based model and the measurement-based model.

In exemplary embodiment B12, the system of any of exemplary embodiments B9-B11, wherein the processors fuse the dynamic-based model and the measurement-based model based on one or more of observation labels and ground-truth labels.

In exemplary embodiment B13, the system of any of exemplary embodiments B9-B12, wherein the time-series measurements include breath measurements, wherein the breath measurements include measurements of pressure and of acceleration.

In exemplary embodiment B14, a non-transitory computer-readable storage medium stores instructions that, when executed, cause a processor to receive sensor data associated with a sensor device that monitors a biological function, the sensor data representing time-series measurement samples of one or more parameters associated with the biological function being monitored by the sensor device; apply a dynamic-based model to the sensor data; apply a measurement-based model to the sensor data; and fuse the dynamic-based model and the measurement-based model.

In exemplary embodiment B15, the non-transitory computer-readable storage medium of exemplary embodiment B14, wherein the processors fuse the dynamic-based model and the measurement-based model based on one or more of observation labels and ground-truth labels.

In exemplary embodiment B16, the non-transitory computer-readable storage medium of any of exemplary embodiments B14 or B15, wherein the processors fuse the dynamic-based model and the measurement-based model based on one or more of observation labels and ground-truth labels.

In exemplary embodiment B17, the non-transitory computer-readable storage medium of any of exemplary embodiments B14-B16, wherein the time-series measurements include breath measurements, wherein the breath measurements include measurements of pressure and of acceleration.

In exemplary embodiment B18, a computing device is configured to perform the methods of any of exemplary embodiments B1-B8.

In exemplary embodiment B19, a system is configured to perform the methods of any of exemplary embodiments B1-B8.

In exemplary embodiment B20, a non-transitory computer readable medium, computing system, or apparatus is configured to perform any of the methods of any of exemplary embodiments B1-B8.

What is claimed is:

1. A method comprising:
receiving sensor data associated with a sensor device that monitors a biological function, the sensor data representing time-series measurement samples of one or more parameters associated with the biological function being monitored by the sensor device, wherein the time-series measurement samples include usable and unusable samples;
extracting data representing two or more features of samples of the time-series measurement samples;
filtering the extracted data, wherein filtering includes eliminating outliers in the extracted data based on an expected outlier ratio; and
training a machine learning algorithm to identify events based on the filtered extracted data.

2. The method of claim 1, wherein eliminating outliers in the extracted feature data includes applying an isolation forest technique to the extracted feature data.

3. The method of claim 1, wherein training the machine learning algorithm includes applying a one-class support vector machine (SVM) technique to the filtered extracted feature data.

4. The method of claim 1, wherein training the machine learning algorithm includes determining clusters of users and applying a one-class support vector machine (SVM) technique to the filtered extracted feature data to determine a machine learning algorithm for each cluster.

5. The method of claim 1, wherein the time-series measurement samples include measurement samples associated with breathing, wherein the measurement samples associated with breathing include measurements of abdominal movement and of acceleration.

6. The method of claim 1, wherein the time-series measurement samples include measurement samples associated with breathing and wherein the features are selected from one or more parameters of the received sensor data, the parameters including relative amplitude, duration, volume of breath, slope, shape, inhalation time, exhalation time, inhalation to exhalation ratio, sample consistency and sample reconstruction error.

7. The method of claim 1, wherein training the machine learning algorithm includes:
receiving labeled sensor data, the labeled sensor data including first labels identifying usable and unusable samples in the labeled sensor data;
assigning second labels to samples in the labeled sensor data, wherein assigning second labels includes applying the machine learning algorithm to the labeled sensor data to detect usable and unusable samples in the labeled sensor data; and
modifying the expected outlier ratio as a function of discrepancies between the first and second labels.

8. The method of claim 7, wherein eliminating outliers in the extracted feature data includes applying an isolation forest technique to the extracted feature data.

9. The method of claim 7, wherein the labeled sensor data includes data labeled as a function of a concurrent alternate measurement of the biological parameters.

10. The method of claim 7, wherein the time-series measurement samples include measurement samples associated with breathing and wherein receiving labeled sensor data includes concurrently capturing measurement samples associated with breathing via the sensor device and via a breath measurement apparatus and labelling the breath measurements captured by the sensor device based on the measurement samples associated with breathing captured by the breath measurement apparatus.

11. A system comprising:
a sensor device configured to monitor at least one biological function;
one or more processors connected to the sensor device; and
memory connected to the one or more processors, wherein the memory includes instructions that, when executed by the one or more processors, cause the one or more processors to:
receive sensor data from the sensor device, the sensor data representing time-series measurement samples of one or more parameters associated with the biological functions being monitored by the sensor device, wherein the time-series measurement samples include usable and unusable samples;
extract data representing two or more features of samples of the time-series measurement samples;
filter the extracted data, wherein filtering includes eliminating outliers in the extracted data based on an expected outlier ratio; and
train a machine learning algorithm to identify events based on the filtered extracted data.

12. The system of claim 11, wherein the sensor device includes a respirator.

13. The system of claim 11, wherein the instructions that cause the one or more processors to train the machine learning algorithm comprise instructions that, when executed, cause the one or more processors to:
receive labeled sensor data, the labeled sensor data including first labels identifying usable and unusable samples in the labeled sensor data;
assign second labels to samples in the labeled sensor data, wherein assigning second labels includes applying the machine learning algorithm to the labeled sensor data to detect usable and unusable samples in the labeled sensor data; and
modify the expected outlier ratio as a function of discrepancies between the first and second labels.

14. The system of claim 13, wherein the time-series measurement samples include measurement samples associated with breathing, and
wherein the instructions that cause the one or more processors to train the machine learning algorithm comprise instructions that, when executed, cause the one or more processors to:
receive labeled sensor data includes concurrently capturing measurement samples associated with breathing via the sensor device and via a breath measurement apparatus; and
label the breath measurements captured by the sensor device based on the measurement samples associated with breathing captured by the breath measurement apparatus.

15. The system of claim 11, wherein the sensor device includes sensors for taking time-series measurements of abdominal movement and of acceleration.

* * * * *